United States Patent
Orlowski

(10) Patent No.: US 9,579,423 B2
(45) Date of Patent: *Feb. 28, 2017

(54) BALLOON CATHETER WITH A SIROLIMUS COATED CATHETER BALLOON FOR CONTROLLED RELEASE OF SIROLIMUS

(75) Inventor: Michael Orlowski, Bonn (DE)

(73) Assignee: Cardionovum S.P.z.o.o (PL)

( * ) Notice: Subject to any disclaimer, the term of this patent is extended or adjusted under 35 U.S.C. 154(b) by 103 days.

This patent is subject to a terminal disclaimer.

(21) Appl. No.: 14/131,583

(22) PCT Filed: Jul. 6, 2012

(86) PCT No.: PCT/EP2012/063301
§ 371 (c)(1),
(2), (4) Date: Jul. 17, 2014

(87) PCT Pub. No.: WO2013/007653
PCT Pub. Date: Jan. 17, 2013

(65) Prior Publication Data
US 2014/0350464 A1    Nov. 27, 2014

(30) Foreign Application Priority Data

Jul. 8, 2011 (WO) ................. PCT/EP2011/003564

(51) Int. Cl.
*A61L 29/08* (2006.01)
*A61L 29/16* (2006.01)
*A61K 31/439* (2006.01)

(52) U.S. Cl.
CPC .............. *A61L 29/08* (2013.01); *A61K 31/439* (2013.01); *A61L 29/085* (2013.01); *A61L 29/16* (2013.01); *A61L 2300/608* (2013.01); *A61L 2420/02* (2013.01); *A61L 2420/08* (2013.01)

(58) Field of Classification Search
None
See application file for complete search history.

(56) References Cited

U.S. PATENT DOCUMENTS

| 2008/0255510 A1 | 10/2008 | Wang | |
| 2010/0076401 A1* | 3/2010 | Von Oepen | A61F 2/958 604/509 |
| 2010/0094410 A1* | 4/2010 | Schomig | A61L 27/34 623/1.46 |

(Continued)

FOREIGN PATENT DOCUMENTS

| EP | 1916006 A1 | 4/2008 |
| EP | 2243501 A1 | 10/2010 |

(Continued)

OTHER PUBLICATIONS

BASF, Kollicoat IR, Feb. 2010.*
(Continued)

*Primary Examiner* — Jianfeng Song
(74) *Attorney, Agent, or Firm* — Clayton, Howarth & Cannon, P.C.

(57) ABSTRACT

The present invention is directed to a catheter balloon of a balloon catheter comprising a coating consisting of or containing at least one fatty acid, oil or fat and sirolimus as well as to the use of these systems and compositions. Optionally a stent is crimped on such a coated catheter balloon. Further, methods for coating the inventive catheter balloons are described.

3 Claims, 2 Drawing Sheets

(56) References Cited

U.S. PATENT DOCUMENTS

2010/0179475 A1* 7/2010 Hoffmann ............... A61L 29/16
                                                    604/103.02
2010/0324645 A1* 12/2010 Stankus ............... A61L 29/085
                                                    623/1.11

FOREIGN PATENT DOCUMENTS

| JP | 2005525411 | 8/2005 |
|---|---|---|
| JP | 2007506775 | 3/2007 |
| JP | 2009511215 | 3/2009 |
| JP | 2009541007 | 11/2009 |
| JP | 2010516307 | 5/2010 |
| WO | WO03092741 | 11/2003 |
| WO | WO2005030182 | 4/2005 |
| WO | WO2007047781 | 4/2007 |
| WO | WO2007047781 A2 | 4/2007 |
| WO | WO2008002434 | 1/2008 |
| WO | WO2008086794 | 7/2008 |
| WO | WO2008139232 A2 | 11/2008 |

OTHER PUBLICATIONS

Posa et al., "Optimization of Drug-Eluting Balloon Use for Safety and Efficacy", Catheterization and Cardiovascular Interventions 76:395-403 (2010), published online May 25, 2010.*
Byrne et al., "A polymer-free dual drug-eluting stent in patients with coronary artery disease", European Heart Journal (2009) 30, 923-931.*
JPO Office Action dated Jan. 5, 2016, Patent Application No. 2014-519507.
English Translation JPO Office Action dated Jan. 5, 2016, Patent Application No. 2014-519507.

* cited by examiner

BALLOON CATHETER WITH A SIROLIMUS COATED CATHETER BALLOON FOR CONTROLLED RELEASE OF SIROLIMUS

CROSS-REFERENCE TO RELATED APPLICATIONS

This application is the National Stage of International Application No. PCT/EP2012/063301, filed Jul. 6, 2012, which was published in English under PCT Article 21(2), which is hereby incorporated by reference in its entirety, which claims priority to International Application No. PCT/EP2011/003564, filed Jul. 8, 2011, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

The invention is directed to a catheter balloon of a balloon catheter comprising a coating consisting of or containing at least one fatty acid, oil or fat and sirolimus. Optionally a stent is crimped on such a coated catheter balloon.

Atherosclerosis is characterized by chronic progressive degeneration of the arteries with progressive changes in the vessel wall. While a healthy artery is elastic and has a smooth inner surface, a diseased artery appears sclerotic and inelastic, thickened and narrowed. It comes to connective-tissue proliferation, intra- and extracellular deposits of cholesterol and fatty acids, calcification as well as an accumulation of collagen and proteoglycans. This narrowing or even blocking of an artery is called stenosis. Most affected areas are sites at which the steady, laminar flow of blood is disturbed, such as vessel branching.

A common and important manifestation of atherosclerosis is coronary heart disease (CHD). Due to the narrowing of the coronary flow, the risk of partial or complete occlusion of arterial branches due to additional thrombus formation consists. A narrowed or blocked coronary artery leads to less blood, and therefore oxygen, supply of the heart muscle, whose proper function is then at risk.

A myocardial infarction occurs if one or more coronary arteries that supply the heart with blood are blocked completely or critically. The heart muscle is not longer provided with enough blood and oxygen and starts processes leading to cell death.

The dilatation of coronary arteries using a balloon catheter and, if necessary, subsequent implantation of a stent, represents one treatment option of stenosis. Meanwhile, balloon dilatation is established as an important method. Narrowing of the coronary vessels, which were caused by deposits of malleable, fatty material, can be remedied by balloon dilatation, so that bypass surgery is unnecessary in many cases.

If balloon dilatation alone does not provide promise of sufficient success, because the vessel wall is already severely compromised due to far advanced atherosclerosis, a stent may be used additionally. The stent remains permanently after removal of the balloon in the vessel wall. Over time, cells of the vessel wall grow around the stent, so that it becomes a support within the arterial wall. Balloon dilatation and stent implantation are often used simultaneously. In 2007 approximately 300,000 coronary interventions were conducted in Germany [van Buuren and Horstkotte. 24. Kardiologe. 2009; 3: 512-518].

Despite these advantages, a stent implantation provides, it also presents clear disadvantages. Stent dilation can cause a tear of the intima, with subsequent hemorrhage between the intima and media (dissection) as well as to mechanical lesion and removal of the endothelium, called denudation, because even a small pressure of ≥3 bar causes the complete destruction of the endothelium. Therefore stent implantation is a traumatic procedure, leading in a multifactorial process to a re-narrowed or restenosed vessel lumen, the so-called in-stent restenosis, which in turn is initiated and prolonged by reactive, complex cellular mechanisms [Kornowski R, Hong M K, Tio F O, Bramwell O, Wu H, Leon M B. In-stent restenosis: contributions of inflammatory responses and arterial injury to neointimal hyperplasia. J Am Coll Cardiol. 1998; 31:224-30].

The development of in-stent-restenosis is divided into three essential phases: inflammation, granulation and remodeling [Schillinger M, Minar E. Restenosis after percutaneous angioplasty: the role of vascular inflammation. Vasc Health Risk Manag. 2005; 1:73-8]. A few minutes after endothelial denudation caused by the stent in the first phase the deposition of platelets occurs on the damaged vessel wall exposed relative to the blood stream and granulocytes with segmented nucleus and other inflammatory cells with release of various growth factors immigrate. In the second phase about 30 percent of stimulated smooth muscle cells with increased proliferation located in the media migrates from the area of media into the intima, where they change their phenotype from the contractile to the secretory type and secrete several matrix proteins in the lumen. Thereby the degree of migration and proliferation of smooth muscle cells depends largely on the degree of initial inflammation. Moreover, in the second phase a starting endothelialization of the stent (re-endothelialization) is to be recorded. If the re-endothelialization is delayed, there is an accumulation of phenotypically modified smooth muscle cells in the vessel lumen. This process appears to be associated with an increased intimal hyperplasia [Grewe P H, Deneke T, Machraoui A, Barmeyer J, Muller K M. Acute and chronic tissue response to coronary stent implantation: pathologic findings in human specimen. J Am Coll Cardiol. 2000; 35:157-63. Schwartz R S, Huber K C, Murphy J G, Edwards W D, Camrud A R, Vlietstra R E, Holmes D R. Restenosis and the proportional neointimal response to coronary artery injury: results in a porcine model. J Am Coll Cardiol. 1992; 19:267-74].

To prevent the induction of restenosis, the use of antiproliferative agents is appropriate. Systemic dose of cytotstatics is not possible in this case, because on one hand effective systemic concentrations administered in the heart are toxic and on the other hand well-tolerated systemic concentrations would be ineffective at the heart [Kolodgie F D, John M, Khurana C, Farb A, Wilson P S, Acampado E, Desai N, Soon-Shiong P, Virmani R. Sustained reduction of in-stent neointimal growth with the use of a novel systemic nanoparticle paclitaxel. Circulation. 2002; 106:1195-8].

Coated catheter balloons are already known from WO 2005/089855 A1. The international patent application WO 2004/028582 A1 discloses multifold balloons which are coated, especially within the folds, with a composition of a pharmacological agent and a contrast medium. A method for spray coating catheter balloons is described in WO 2004/006976 A1.

Fatty acids are water-insoluble, oily or fatty substances which represent, besides water, enzymes and carbohydrates, important biomolecules, that serve either in the form of triacylglycerins as combustible for the winning of chemical energy and can be stored or which ensure the formation and the continuance of the cell in the form of membrane constituting compounds such as phosphoglycerids and sphingolipids.

EP 0 404 683 B1 describes the utilization of fatty acids on medical surfaces, which are in contact with blood. The fatty acids and especially the linoleic acid are bound covalently to the used hydrophilic polymer for the improvement of its hemocompatibility. Mentioned examples of use are artificial organs, dialyzers, blood filters and catheters.

WO 03 039 612 A also refers to the known antithrombotic and antiproliferative effect of the unsaturated fatty acids on the cardiovascular system and describes for the first time a coating of stents with purchasable oils such as olive oil, sun flower oil, palm-oil and fish oil and especially of cod-liver oil. The fluid oils used are utilized as antithrombotic coating.

The object of the present invention is to provide a matrix for controlled release of sirolimus during dilatation. Thus object of the present invention is to provide a sirolimus eluting catheter balloon which is highly efficient in the treatment and prevention of restenosis.

It is further an objective of the present invention to apply sirolimus onto a catheter balloon in such a manner that a coating is created which can be effectively transferred to the vessel wall but is easily detached from the balloon during inflation so that a therapeutic effect concerning reduction of restenosis can be achieved.

It has surprisingly been found that certain naturally occurring fatty acids, oils and fats and especially free fatty acids and more preferably free unsaturated fatty acids adhere sufficiently strong to the surface of a catheter balloon, so that the majority of the biological coating remains on the surface when the balloon catheter is introduced into a vessel or other body cavity of a patient. When the catheter balloon is positioned at the treatment site in the vessel of the patient, the at least one fatty acid, oil or fat together with sirolimus contained in the coating, too, are transferred directly into the tissue being treated. This is caused by the lipophilic, adsorbing effect of at least one fatty acid, oil or fat and especially free unsaturated fatty acids and more preferably free omega fatty acids. The natural binding capacity and cellular uptake of the at least one fatty acid, oil or fat causes an unexpected effect on sirolimus permeation during release to the treated size of the vessel. The use of a mixture of sirolimus with the at least one fatty acid, oil or fat (subsequently called fatty acid-drug complex) improves considerably the penetration of sirolimus into the treated tissue by the natural absorption of the fatty acid-drug complex. Since the biological binding capacity of the fatty acid-drug complex is very high for many tissue types, the fatty acid-drug complex is easily detached from the surface of the catheter balloon and transferred to the treated tissue. The fatty acid-drug complex remains chemically intact. Furthermore, no additional biochemical or physiological reactions are needed to detach the coating comprising the at least one fatty acid, oil or fat especially free unsaturated fatty acids and more preferably free omega fatty acids, from the balloon surface. Upon dilatation of the balloon catheter, the fatty acid-drug complex is transferred to the vessel wall during vasodilation because the fatty acid-drug complex on the balloon surface comes into contact with the vessel wall. This direct transfer to the treatment site limits systemic effects of sirolimus but achieves desired local effects.

Surprisingly, experimental data have further shown that the use of at least one fatty acid, oil or fat and especially free unsaturated fatty acids and more preferably free omega 3 and 6 fatty acids reduces the probability of inflammation which may be induced by dilatation of a catheter balloon and optionally stent implantation. It is known that specific fatty acids, oils or fats, such as omega fatty acids and especially omega-3 and omega-6 fatty acids, are not only well tolerated by the body of a patient but also have themselves a physiological and therapeutical effect. Such fatty acids, oils or fats, such as omega fatty acids and especially omega-3 and omega-6 fatty acids, reduce commonly occurring inflammation, which is caused by the contact under pressure of the catheter balloon with the tissue to be treated. The mixture of the active agent with such a fatty acid, oil or fat especially free unsaturated fatty acids and more preferably free omega fatty acids reduces effectively the occurrence of inflammation. This in turn leads to an unexpected improvement of cellular uptake of sirolimus into the tissue to be treated. The fatty acid-drug complex, further enhances the cellular uptake of sirolimus, because during balloon dilatation the sirolimus coating is smeared to the vessel wall.

The invention is directed to a catheter balloon comprising a coating with at least one fatty acid, oil or fat, such as free unsaturated fatty acids, preferably free omega fatty acids and especially omega-3 and omega-6 fatty acids and sirolimus. Moreover the present invention relates to balloon catheters comprising such a catheter balloon coated in accordance to the present invention.

Any conventional catheter balloon, bifurcation balloon, angioplasty balloons, valvuloplasty balloon as well as folded balloon or special catheter balloon may be used as a catheter balloon of the present invention. The term "catheter balloon" respectively "conventional catheter balloon" refers also to such dilatable catheter balloons which usually serve to place a stent by means of dilation. Furthermore, it refers also to non-dilatable catheter balloons for stent placement suitable for self-expanding stents and carrying a removable wrapper on the stent for avoiding premature stent expansion.

Bifurcation balloons refer to catheter balloons for treating a bifurcation of a vessel, especially of a blood vessel. Such balloons may have two arms or consist of two combined or two separate balloons being used contemporarily or consecutively for the treatment of a vessel bifurcation respectively the placement of one or two stents in a vessel bifurcation or in the immediate proximity of a vessel bifurcation.

Folded balloons refer to balloons as described for example in EP 1189553 B1, EP 0519063 B1, WO 03/059430 A1 and WO 94/23787 A1, having "folds" in the compressed state of the balloon that open at least partially when expanding the balloon.

Special balloons refer especially to balloons with pores, particularly micropores, allowing liquids and solutions to pass through during expansion or on applying pressure. Such a balloon with micropores is disclosed in EP 383 429 A. Moreover, the term special balloon refers to balloons with an especially designed surface with microneedles as described in WO 02/043796 A2 or to a catheter balloon as disclosed in WO 03/026718 A1 with a micro raw or nano raw surface for embedding active agents with or without carrier substances.

Valvuloplasty balloons are used for dilatation of a pathologically narrowed heart valve, wherein the balloon which is attached to a catheter is pushed to the constriction and subsequently dilatated.

The term balloon or catheter balloon basically refers to every expandable and recompressible as well as temporarily inflatable medical device usually used together with a catheter. The catheter balloon can consist of current materials, especially polymers as described further down, and particularly of polyamide as e.g. PA 12, polyester, polyurethane, polyacrylates, polyethers and so on.

The coated balloons according to the invention or a balloon catheter comprising such a balloon are suitable to prevent or to reduce restenosis. The use of a coated balloon according to the invention is thereby not limited to a first treatment of stenotic vessels but they are also particularly useful to treat or prevent successfully an occurring restenosis (e.g. in-stent-restenosis) and a recurrent re-occlusion.

The coated balloons according to the invention can be used without a stent or with a crimped stent. The stent may consist likewise of common materials as for example medical stainless steel, titanium, chrome, vanadium, tungsten, molybdenum, gold, Nitinol, magnesium, iron, alloys of aforesaid metals as well as polymeric material as e.g. chitosan, heparanes, polyhydroxybutyrates (PHB), polyglycerides, polylactides and copolymers of the aforesaid materials.

The present invention relates to a catheter balloon coated with sirolimus and at least one fatty acid, oil or fat such as omega fatty acids and especially omega-3 and omega-6 fatty acids. Preferably the coated catheter balloons according to the invention are used without an attached stent, but the use with a crimped stent is possible, too. If a crimped stent is used the stent may be bare or likewise coated, whereby the stent may have a different coating and also a different active agent than the coating of the catheter balloon.

The term "coating" as used herein shall comprise not only a coating of the surface of the catheter balloon but also a filling or coating of folds, cavities, pores, microneedles or other fillable spaces on, between or in the balloon material.

The substances suitable for the coating of the balloon surfaces of balloon catheter, comprise i.a. oils, fats, and fatty acids, which are described in more detail below.

It is preferred if the at least one oil is chosen from the group comprising or consisting of olive oil, hemp oil, corn oil, walnut oil, canola oil, soybean oil, sunflower oil, poppyseed oil, safflower oil, wheat germ oil, grape seed oil, evening primrose oil, borage oil, black cumin oil, chia, algae oil, fish oil, cod liver oil and/or mixtures of the aforementioned oils. Especially suitable are mixtures of the pure unsaturated compounds.

It is more preferred to use pure synthetic or natural fatty acids, while the use of fatty acid esters or salts of fatty acids or lipids or glycerides containing covalently bound fatty acids are not preferred for the catheter balloon coating according to the invention. The inventors found that only free fatty acids and especially free unsaturated fatty acids are able to achieve the inventive effect of restenosis prophylaxis and restenosis treatment while salts and esters and amides of the fatty acids are not able to achieve such an effective restenosis treatment or prevention. Consequently, fatty acid esters and fatty acid salts or other compounds obtained by reacting the carboxylat group of the fatty acid covalently with other substances such as amines or alcohols or acid halogenides are not used and shall not be used for the coating according to the present invention. Moreover also fatty aldehydes and fatty alcohols obtained by reduction of the fatty acid are not suitable for the present invention. Therefore the inventors found that the use of free fatty acids and especially free unsaturated fatty acids are essential to obtain the inventive effect.

As used herein, the term "fatty acid" refers to compounds of the general formula R—COOH, wherein R is the carbon chain of the fatty acid which preferably contains double and/or triple bonds and more preferably between 1 and 5 double bonds. The carbon chain R preferably contains between 9 and 29, more preferably between 11 and 27, still more preferably between 13 and 25, still more preferably between 15 and 23, and most preferably between 17 and 21 carbon atoms. Preferably these carbon atoms form a linear unbranched chain.

Preferably the unsaturated fatty acids are chosen from the group, which comprises omega-3, omega-6, omega-7 and omega-9 fatty acids. Omega-3, omega-6, and omega-9 fatty acids are more preferred and omega-3 as well as omega-6 fatty acids are even more preferred, while omega-3 fatty acids are most preferred.

Omega 3 fatty acids (also called ω-3 fatty acids or n-3 fatty acids) are a class of essential polyunsaturated fatty acids with the last double bond in the third carbon position from the methyl terminal end. Analogous omega-6 fatty acids are a class of essential polyunsaturated fatty acids with the initial double bond in the sixth carbon position from the methyl group.

The following tables 1 to 4 show a listing of the omega fatty acids, which are preferably used in the present invention.

TABLE 1 omega-3 fatty acids

| Common name | Lipid name | Chemical name |
| --- | --- | --- |
| Hexadecatrienoic acid (HTA) | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (SDA) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Heneicosapentaenoic acid (HPA) | 21:5 (n-3) | all-cis-6,9,12,15,18-heneicosapentaenoic acid |
| Docosapentaenoic acid (DPA) | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-tetracosapentaenoic acid |
| Tetracosahexaenoic acid (Nisinic acid) | 24:6 (n-3) | all-cis-6,9,12,15,18,21-tetracosahexaenoic acid |

Further preferred omega-3 fatty acids are selected from the group consisting of or comprising: eicosapentaenoic acid (EPA C20:5), Eicosatrienoic acid (ETE C20:3), Eicosatetraenoic acid (ETA C20:4), docosahexaenoic acid (DHA C22:6), hexadecatrienoic acid (HTAC16:3), stearidonic acid (SDA C18:4), heneicosapentaenoic acid (HPA C21:5), docosapentaenoic acid (DPA C22:5), tetracosapentaenoic acid, tetracosahexaenoic acid and α-linolenic acid (ALA C18:3) as well as mixtures of the aforementioned fatty acids. These mixtures comprise especially mixtures of the pure unsaturated compounds. Especially preferred is the omega-3 fatty acid α-linolenic acid (ALA C18:3) (see table 1).

TABLE 2

| Common name | Lipid name | Chemical name |
|---|---|---|
| omega-6 fatty acids | | |
| Linoleic acid (LA) | 18:2 (n-6) | all-cis-9,12-octadecadienoic acid |
| Gamma-linolenic acid (GLA) | 18:3 (n-6) | all-cis-6,9,12-octadecatrienoic acid |
| Eicosadienoic acid | 20:2 (n-6) | all-cis-11,14-eicosadienoic acid |
| Dihomo-gamma-linolenic acid (DGLA) | 20:3 (n-6) | all-cis-8,11,14-eicosatrienoic acid |
| Arachidonic acid (AA) | 20:4 (n-6) | all-cis-5,8,11,14-eicosatetraenoic acid |
| Docosadienoic acid | 22:2 (n-6) | all-cis-13,16-docosadienoic acid |
| Adrenic acid | 22:4 (n-6) | all-cis-7,10,13,16-docosatetraenoic acid |
| Docosapentaenoic acid | 22:5 (n-6) | all-cis-4,7,10,13,16-docosapentaenoic acid |
| Tetracosatetraenoic acid | 24:4 (n-6) | all-cis-9,12,15,18-tetracosatetraenoic acid |
| Tetracosapentaenoic acid | 24:5 (n-6) | all-cis-6,9,12,15,18-tetracosapentaenoic acid |
| Calendic acid | 18:3 (n-6) | 8E,10E,12Z-octadecatrienoic acid |

Further preferred omega-6 fatty acids are selected from the group consisting of or comprising: linolenic acid (LA C18:2), gamma-linolenic acid (GLA C18:3), Eicosadienoic acid (C20:2), dihomo-gamma-linolenic acid (DGLA 20:3), arachidonic acid (AA C20:4), docosadienoic acid (C22:2), docosapentaenoic acid (C22:5), tetracosatetraenoic acid (24:4) and calendic acid (18:3) as well as mixtures of the aforementioned fatty acids (see table 2).

TABLE 3

| Common name | Lipid name | Chemical name |
|---|---|---|
| omega-7 fatty acids | | |
| none | 12:1 (n-7) | 5-Dodecenoic acid |
| none | 14:1 (n-7) | 7-Tetradecenoic acid |
| Palmitoleic acid | 16:1 (n-7) | 9-Hexadecenoic acid |
| Vaccenic acid | 18:1 (n-7) | 11-Decenoic acid |
| Paullinic acid | 20:1 (n-7) | 13-Eicosenoic acid |
| none | 22:1 (n-7) | 15-Docosenoic acid |
| none | 24:1 (n-7) | 17-Tetracosenoic acid |

Further preferred omega-7 fatty acids are chosen from the group consisting of: 5-dodecenoic acid, 7-tetradecenoic acid, palmitoleic acid, vaccenic acid, paullinic acid, 15-docosenoic acid and 17-tetracosenoic acid.

TABLE 4

| Common name | Lipid name | Chemical name |
|---|---|---|
| omega-9 fatty acids | | |
| oleic acid | 18:1 (n-9) | 9-octadecenoic acid |
| Elaidic acid | 18:1 (n-9) | (E)-octadec-9-enoic acid |
| eicosenoic acid | 20:1 (n-9) | cis-11-eicosenoic acid |
| mead acid | 20:3 (n-9) | 5,8,11-eicosatrienoic acid |
| erucic acid | 22:1 (n-9) | 13-docosenoicacid |
| nervonic acid | 24:1 (n-9) | 15-tetracosenoic acid |

Further preferred omega-9 fatty acids are chosen from the group consisting of: oleic acid, elaidic acid, eicosenoic acid, mead acid, erucic acid and nervonic acid.

Fish oil and cod-liver oil mainly contain eicosapentaenoic acid (EPA C20:5) and docosahexaenoic acid (DHA C22:6) besides of little α-linolenic acid (ALA C18:3). Omega-3 fatty acids can be found not only in fish oil, but also in vegetable oils. Further unsaturated fatty acids, such as the omega-6 fatty acids, are present in oils of herbal origin, which here partly constitute a higher proportion than in animal fats. Hence different vegetable oils such as linseed oil, walnut oil, flax oil, evening primrose oil with accordingly high content of essential fatty acids are recommended as especially high-quality and valuable edible oils. Especially linseed oil represents a valuable supplier of omega-3 and omega-6 fatty acids and is known for decades as high-quality edible oil.

The following table 5 shows a listing of the fatty acid components in different oils, which are preferably used in the present invention.

TABLE 5

| | Oleic acid (C 18:1) omega-9 | Linoleic acid (C 18:2) omega-6 | Linolenic acid (C 18:3) omega-3 | Eicosapentaenoic acid (C 20:5) omega-3 | Docosahexaenoic acid (C 22:6) omega-3 |
|---|---|---|---|---|---|
| Fatty acid components of different oils | | | | | |
| Oil species | | | | | |
| Olive oil | 70 | 10 | 0 | 0 | 0 |
| Corn oil | 30 | 60 | 1 | 0 | 0 |
| Linseed oil | 20 | 20 | 60 | 0 | 0 |
| Cod-liver oil | 25 | 2 | 1 | 12 | 8 |
| Fish oil | 15 | 2 | 1 | 18 | 12 |

Further unsaturated fatty acids which can be used in accordance with the present invention can be selected from the following tables 6 to 8:

TABLE 6

| Systematic name | Trivial name | Short form |
|---|---|---|
| Monoolefinic fatty acids | | |
| cis-9-tetradecenoic acid | myristoleic acid | 14:1(n-5) |
| cis-6-octadecenoic acid | petroselinic acid | 18:1(n-12) |
| cis-9-eicosenoic acid | gadoleinic acid | 20:1(n-11) |
| t9-octadecenoic acid | elaidinic acid | |
| t11-octadecenoicacid | t-vaccenic acid | |
| t3-hexadecenoic acid | | trans-16:1 (n-13) |

TABLE 7

| Systematic name | Trivial name | Short form |
|---|---|---|
| Poly-unsaturated fatty acids | | |
| 8,11,14,17-eicosatetraenoic acid | — | 20:4(n-3) |
| 9c,11t,13t-eleostearinoic acid | | |
| 8t,10t,12c-calendinoic acid | | |
| 9c,11t,13c-catalpicoic acid | | |

TABLE 7-continued

Poly-unsaturated fatty acids

| Systematic name | Trivial name | Short form |
|---|---|---|
| 4,7,9,11,13,16,19-docosahepta-decanoic acid | stellaheptaenic acid | |
| | taxolic acid | all-cis-5,9-18:2 |
| | pinolenic acid | all-cis-5,9,12-18:3 |
| | sciadonic acid | all-cis-5,11,14-20:3 |

TABLE 8

Acetylenic fatty acids

| Systematic name | Trivial name |
|---|---|
| 6-octadecynoic acid | taririnic acid |
| t11-octadecen-9-ynoic acid | santalbinic or ximeninic acid |
| 9-octadecynoic acid | stearolinic acid |
| 6-octadecen-9-ynoic acid | 6,9-octadeceninic acid |
| t10-heptadecen-8-ynoic acid | pyrulinic acid |
| 9-octadecen-12-ynoic acid | crepenynic acid |
| t7,t11-octadecadiene-9-ynoic acid | heisterinic acid |
| t8,t10-octadecadiene-12-ynoic acid | — |
| 5,8,11,14-eicosatetraynoic acid | ETYA |

In the present invention preferably unsaturated fatty acids, more preferably polyunsaturated fatty acids, even more preferably omega-3, omega-6, omega-7 or omega-9 fatty acids, still more preferably omega-3 and omega-6 fatty acids and most preferably omega-3 fatty acids are used.

Within the most preferred omega-3 fatty acids the following species are preferred: α-Linolenic acid (ALA), Stearidonic acid (SDA), Eicosatrienoic acid (ETE), Eicosatetraenoic acid (ETA), Eicosapentaenoic acid (EPA), Docosapentaenoic acid (DPA) and Docosahexaenoic acid (DHA).

Within the preferred omega-6 fatty acids the following species are preferred: Linoleic acid (LA), Gamma-linolenic acid (GLA), Eicosadienoic acid, Dihomo-gamma-linolenic acid (DGLA), Arachidonic acid (AA), Docosadienoic acid, Adrenic acid and Docosapentaenoic acid.

Within the omega-7 fatty acids the following species are preferred: vaccenic acid and paullinic acid.

Within the omega-9 fatty acids the following species are preferred: oleic acid, elaidic acid, eicosenoic acid and mead acid.

According to the invention it is preferred that the surface of the balloon of a balloon catheter is coated with at least one fatty acid, oil or fat and preferably at least one fatty acid which contains an amount of unsaturated fatty acids of at least 38 percent by weight. It is further preferred if the at least one fatty acid, oil or fat and preferably at least one fatty acid used in the coating according to the invention contains an amount of at least 52 percent by weight, preferably of 59 percent by weight, still preferred 68 percent by weight and most preferably 76 percent by weight of unsaturated fatty acids.

The biocompatible coating comprising at least one fatty acid, especially free unsaturated fatty acids and more preferably free omega fatty acids or fat on the balloon surface provides the necessary blood compatibility of the balloon catheter and is at the same time a suitable carrier for sirolimus. According to the invention sirolimus is dissolved, suspended, emulsified or dispersed in the at least one fatty acid, oil or fat especially in the at least one free unsaturated fatty acid and more preferably free omega fatty acid, for the application of the coating to the balloon surface. The use of at least one fatty acid, oil or fat such as omega fatty acids and especially omega-3 and omega-6 fatty acids is particularly advantageous in combination with less lipophilic active agents such as sirolimus since then the lipophilicity of the entire coating is increased. Thus it can be ensured that also hydrophilic or less lipophilic active agents adhere to a sufficient extent during dilatation of the primarily lipophilic artery wall and subsequently penetrate into the tissue. The lipophilic balloon coating also protects sirolimus, a relatively hydrophilic active agent, from premature release by the blood stream during insertion of the catheter. The lipophilic coating of at least one fatty acid, especially free unsaturated fatty acids and more preferably free omega fatty acids, oil or fat containing sirolimus is at least partially transferred to the vessel wall, where it can form a depot from which sirolimus can be transmitted to and into the cells.

Thus the lipophilic coating solves at least two problems, on the one hand sirolimus is protected against premature detachment during insertion of the catheter balloon and on the other hand after dilation a matrix for sirolimus is formed on the vessel wall, from which sirolimus can be delivered to the cells over a certain period, wherein said lipophilic matrix is physiologically compatible and can be degraded by natural means, preferably without forming harmful metabolites. For treatment of heavily calcified stenoses the lipophilic matrix also contributes to the reduction of inflammatory processes and for the transport of at least one active agent deep into the dilated stenosis and thus provides an improved sirolimus delivery.

Sirolimus is used in regard to the present invention as the active agent. Sirolimus may be used individually or combined with other antiproliferative, antimigrative, antiangiogenic, antirestenotic, cytostatic or cytotoxic active substances having same or different concentration. These active agents can be dissolved, emulsified, suspended or dispersed in the at least one fatty acid, such as omega fatty acid and especially omega-3 and omega-6 fatty acid, oil or fat, so that only one layer exists on the surface of the balloon. Such an inclusion of sirolimus and optionally further active agents ensures that a short-term and controlled release of the active agents from the matrix takes place by the balloon dilatation during vasodilation. Further, there is the possibility, that sirolimus or the combination of sirolimus and at least one further active agent is applied to the surface after coating of the catheter balloon with the at least one fatty acid, oil or fat, especially free unsaturated fatty acid and more preferably free omega fatty acid, which will then absorb sirolimus optionally in combination with a further active agent. However preferably sirolimus is used as sole active agent in the balloon coating and is preferably not combined with other active agents as mentioned below.

It is a possible embodiment of the present invention that the at least one further active agent used in combination with sirolimus is selected from the group consisting of or comprising: biolimus A9, myolimus, novolimus, pimecrolimus, tacroliums, temsirolimus, zotarolimus, Everolimus, ridaforolimus, somatostatin, roxithromycin, dunaimycin, ascomycin, bafilomycin, erythromycin, midecamycin, josamycin, concanamycin, clarithromycin, troleandomycin, folimycin, cerivastatin, simvastatin, lovastatin, fluvastatin, rosuvastatin, atorvastatin, pravastatin, pitavastatin, vinblastine, vincristine, vindesine, vinorelbine, etoposide, teniposide, nimustine, carmustine, lomustine, cyclophosphamide, 4-hydroxycyclophosphamide, estramustine, melphalan, ifosfamide, trofosfamide, chlorambucil, bendamustine, dacarbazine, busulfan, procarbazine, treosulfan, temozolomide, thiotepa, daunorubicin, doxorubicin, aclarubicin, epirubicin, mitoxantrone, idarubicin, bleomycin, mitomycin, dactinomycin, methotrexate, fludarabine, fludarabine-5'-dihydrogenphosphate, cladribine, mercaptopurine, thioguanine, cytarabine, fluorouracil, gemcitabine, capecitabine, docetaxel, carboplatin, cisplatin, oxaliplatin, amsacrine, irinotecan, topotecan, hydroxycarbamide, miltefosine, pentostatin, aldesleukin, tretinoin, asparaginase, pegaspargase, anastrozole, exemestane, letrozole, formestane, aminoglutethimide, adriamycin, azithromycin, spiramycin, cepharantin, smc proliferation inhibitor-2w, epothilone A and B, mitoxantrone, azathioprine, mycophenolatmofetil, c-myc-antisense, b-myc-antisense, betulinic acid, camptothecin, PI-88 (sulfated oligosaccharide), melanocyte stimulating hormone (α-MSH), activated protein C, IL-1β inhibitor, thymosine α-1, fumaric acid and its esters, calcipotriol, tacalcitol, lapachol, β-lapachone, podophyllotoxin, betulin, podophyllic acid 2-ethylhydrazide, molgramostim (rhuGM-CSF), peginterferon α-2b, lenograstim (r-HuG-CSF), filgrastim, macrogol, dacarbazine, basiliximab, daclizumab, selectin (cytokine antagonist), CETP inhibitor, cadherines, cytokinin inhibitors, COX-2 inhibitor, NFkB, angiopeptin, ciprofloxacin, camptothecin, fluoroblastin, monoclonal antibodies, which inhibit the muscle cell proliferation, bFGF antagonists, probucol, prostaglandins, 1,11-dimethoxycanthin-6-one, 1-hydroxy-11-methoxycanthin-6-one, scopoletin, colchicine, NO donors, pentaerythritol tetranitrate, syndnoeimines, S-nitrosoderivatives, tamoxifen, staurosporine, β-estradiol, α-estradiol, estriol, estrone, ethinylestradiol, fosfestrol, medroxyprogesterone, estradiol cypionates, estradiol benzoates, tranilast, kamebakaurin and other terpenoids, which are applied in the therapy of cancer, verapamil, tyrosine kinase inhibitors (tyrphostines), cyclosporine A, paclitaxel and derivatives thereof, 6-α-hydroxy-paclitaxel, baccatin, taxotere, synthetically produced as well as from native sources obtained macrocyclic oligomers of carbon suboxide (MCS) and derivatives thereof, mofebutazone, acemetacin, diclofenac, lonazolac, dapsone, o-carbamoylphenoxyacetic acid, lidocaine, ketoprofen, mefenamic acid, piroxicam, meloxicam, chloroquine phosphate, penicilamine, tumstatin, avastin, hydroxychloroquine, auranofin, sodium aurothiomalate, oxaceprol, celecoxib, P-sitosterin, ademetionine, myrtecaine, polidocanol, nonivamide, levomenthol, benzocaine, aescin, ellipticine, D-24851 (Calbiochem), colcemid, cytochalasin A-E, indanocine, nocodazole, S 100 protein, bacitracin, vitronectin receptor antagonists, azelastine, guanidyl cyclase stimulator, tissue inhibitor of metal proteinase-1 and -2, free nucleic acids, nucleic acids incorporated into virus transmitters, DNA and RNA fragments, plasminogen activator inhibitor-I, plasminogen activator inhibitor-2, antisense oligonucleotides, VEGF inhibitors, IGF-1; antibiotics, cefadroxil, cefazolin, cefaclor, cefotaxim, tobramycin, gentamycin, penicillins, dicloxacillin, oxacillin, sulfonamides, metronidazol, antithrombotics, argatroban, aspirin, abciximab, synthetic antithrombin, bivalirudin, coumadin, enoxaparin, desulphated and N-reacetylated heparin, tissue plasminogen activator, GpIIb/IIIa platelet membrane receptor, factor $X_a$ inhibitor antibodies, heparin, hirudin, r-hirudin, PPACK, protamin, sodium salt of 2-methylthiazolidine-2,4-dicarboxylic acid, prourokinase, streptokinase, warfarin, urokinase, vasodilators, dipyramidole, trapidil, nitroprussides, PDGF antagonists, triazolopyrimidine and seramin, ACE inhibitors, captopril, cilazapril, lisinopril, enalapril, losartan, thio-protease inhibitors, prostacyclin, vapiprost, α, β and γ interferon, histamine antagonists, serotonin blockers, apoptosis inhibitors, apoptosis regulators, halofuginone, nifedipine, tocopherol, vitamin B1, B2, B6 and B12, folic acid, tranilast, molsidomine, tea polyphenols, epicatechin gallate, epigallocatechin gallate, Boswellinic acids and derivatives thereof, leflunomide, anakinra, etanercept, sulfasalazine, etoposide, dicloxacillin, tetracycline, triamcinolone, mutamycin, procainamid, retinoic acid, quinidine, disopyramide, flecamide, propafenone, sotalol, amidorone, natural and synthetically produced steroids, inotodiol, maquiroside A, ghalakinoside, mansonine, strebloside, hydrocortisone, betamethasone, dexamethasone, non-steroidal substances, fenoprofen, ibuprofen, indomethacin, naproxen, phenylbutazone, antiviral agents, acyclovir, ganciclovir, zidovudine, antimycotics, clotrimazole, flucytosine, griseofulvin, ketoconazole, miconazole, nystatin, terbinafine, antiprozoal agents, chloroquine, mefloquine, quinine, natural terpenoids, hippocaesculin, barringtogenol-C21-angelate, 14-dehydroagrostistachin, agroskerin, agrostistachin, 17-hydroxyagrostistachin, ovatodiolids, 4,7-oxycycloanisomelic acid, baccharinoids B1, B2, B3 and B7, tubeimoside, bruceanol A, B and C, bruceantinoside C, yadanziosides N and P, isodeoxyelephantopin, tomenphantopin A and B, coronarin A, B, C and D, ursolic acid, hyptatic acid A, zeorin, iso-iridogermanal, maytenfoliol, effusantin A, excisanin A and B, longikaurin B, sculponeatin C, kamebaunin, leukamenin A and B, 13,18-dehydro-6-α-senecioyloxychaparrin, taxamairin A and B, regenilol, triptolide, moreover cymarin, apocymarin, aristolochic acid, anopterin, hydroxyanopterin, anemonin, protoanemonin, berberine, cheliburin chloride, cictoxin, sinococuline, bombrestatin A and B, cudraisoflavone A, curcumin, dihydronitidine, nitidine chloride, 12-β-hydroxypregnadiene-3,20-dione, bilobol, ginkgol, ginkgolic acid, helenalin, indicine, indicine-N-oxide, lasiocarpine, inotodiol, glycoside 1a, podophyllotoxin, justicidin A and B, larreatin, malloterin, mallotochromanol, isobutyrylmallotochromanol, maquiroside A, marchantin A, maytansine, lycoridicin, margetine, pancratistatin, liriodenine, oxoushinsunine, aristolactam-AII, bisparthenolidine, periplocoside A, ghalakinoside, ursolic acid, deoxypsorospermin, psychorubin, ricin A, sanguinarine, manwu wheat acid, methylsorbifolin, spatheliachromen, stizophyllin, mansonine, strebloside, akagerine, dihydrousambarensine, hydroxyusambarine, strychnopentamine, strychnophylline, usambarine, usambarensine, berberine, liriodenine, oxoushinsunine, daphnoretin, lariciresinol, methoxylariciresinol, syringaresinol, umbelliferon, afromoson, acetylvismione B, desacetylvismione A, vismione A, vismione B and sulfur containing amino acids as well as salts and/or mixtures of the aforementioned active agents.

As a very prosperous active agent for the purpose of restenosis prophylaxis is rapamycin (syn. sirolimus) a hydrophilic macrolid antibiotic. This active agent is especially utilized in transplantation medicine as immunosuppressive, wherein contrary to other immunosuppressive active agents sirolimus also inhibits tumor formation. As after transplantation an increased risk of tumor formation exists for the patient, the administration of sirolimus is advantageous because other immunosuppressives such as cyclosporin A can even promote tumor formation as is known.

The mechanism of action of sirolimus is not yet known in detail but it is attributed especially to the complex formation with the protein mTOR (mammalian target of rapamycin) a phosphatidylinositol-3 kinase of 282 kD. As mTOR is responsible for a series of cytokine-mediated signal transduction paths i.a. also for signal paths which are necessary for cell division besides the immunosuppressive effect, it has also antiphlogistic, antiproliferative and even antimycotic properties.

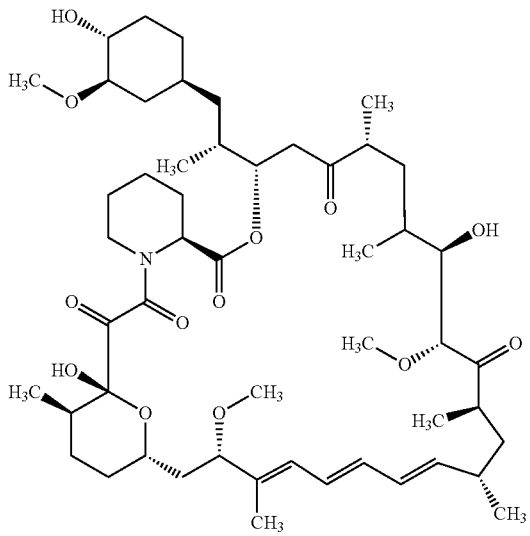 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)CC(C)[C@@H](O)[C@@H](OC)C(=O)[C@H](C)C[C@H](C)/C=C/C=C/C=C/1C]

IUPAC Name:
[3S-[3R*[E(1S*,3S*,4S*)],4S*,5R*,8S*,9E,12R*,14R*, 15S*,16R*,18S*,19S*,26aR*]]-5,6,8,11,12,13,14,15,16,17, 18,19,24,25,26,26a-hexadecahydro-5,19-dihydroxy-3-[2-(4-hydroxy-3-methoxycyclohexyl)-1-methylethenyl]-14, 16-dimethoxy-4,10,12,18-tetra methyl-8-(2-propenyl)-15, 19-epoxy-3H-pyrido[2,1-c][1,4]-oxaazacyclotricosine-1,7, 20,21(4H,23H)-tetron monohydrate.

Proliferation is interrupted in the late G1 phase by stopping the ribosomal protein synthesis. Compared to other antiproliferative active agents sirolimus's mechanism of action can be pointed out as special likewise paclitaxel but which is strongly hydrophobic. Moreover, the immunosuppressive and antiphlogistic effects as described above are more than advantageous because also the extent of inflammatory reactions and of the total immune response as their premature control after stent implantation is decisive for the further success.

Thus, sirolimus has all of the necessary conditions for the utilization against stenosis and restenosis. Sirolimus limited shelf life on or in an implant is to be mentioned as an additional advantage in comparison to paclitaxel because necessarily the active agent has to be effective in the first decisive weeks after angioplasty and eventually stent implantation. Consequently, the endothelial cell layer which is important for the completion of a healthy healing process can completely grow over the lesion and optionally over the stent and integrate it into the vessel wall.

Sirolimus itself is no warrant for an optimal prophylaxis of restenosis. The sirolimus-eluting catheter balloon has to meet the requirements in its entirety. Besides the determination of dosing the sirolimus elution has to be effective during the short time of dilatation. The sirolimus elution as well as the rate of sirolimus elution do not depend only on the physical and chemical properties of sirolimus but depends also on the properties of the utilized matrix and the interactions of the matrix and sirolimus.

Sirolimus is preferably applied on the surface of the catheter balloon in a pharmacologically active concentration of 0.1-50 μg/mm² of the balloon surface, more preferred 1.0-15.0 μg/mm² of the balloon surface, further preferred 2.0-8.0 mg/cm² of the balloon surface and especially preferred 2.5-6.0 mg/cm² of the balloon surface. A second active substance may be applied in a similar concentration in the same layer of the coating or in a different layer of the balloon coating. The melting point of the at least one fatty acid, oil or fat, such as omega fatty acids and especially omega-3 and omega-6 fatty acids, is preferably lower than or equal to 37° C., so that the at least one fatty acid, oil or fat is in a molten state after insertion into the vessel.

It is further preferred if the at least one fatty acid, oil or fat has a melting point higher than 10° C., preferably higher than 15° C. and even more preferred higher than 20° C. and especially preferred higher than 30° C. It is most preferably, when said at least one fatty acid, oil or fat, especially the free fatty acids having 18-22 C-atoms, is in a liquid state at room temperature, particular at 20° C.

It is also possible to apply one or more additional adjuvants as a carrier or second matrix substance to the surface of the catheter balloon according to the invention. There are, for example, contrast agents or contrast media analogs, surfactants, emulsifier, preferably a polyethoxylated surfactant or a polyethoxylated emulsifier and biologically compatible organic substances that improve the coating properties and increase the uptake of sirolimus into the vessel, such as sugar and proteins like albumin or resins especially dammar, mastic, rosin, or shellac.

Particularly preferred as a matrix for the sirolimus coating of a catheter balloon is a combination of at least one fatty acid, oil or fat with shellac and especially of an unsaturated fatty acid, and even more preferably free fatty acids having 18-22 C-atoms, as mentioned above and shellac.

One preferred embodiment is therefore a catheter balloon of a balloon catheter coated with at least one fatty acid, oil or fat, especially with at least one free unsaturated fatty acid and more preferably free omega fatty acid, sirolimus and additionally with at least one further excipient. It is particularly preferred that the at least one excipient is shellac. Therefore one preferred embodiment is a catheter balloon of a balloon catheter coated with a free omega fatty acid, especially omega-3 and omega-6 fatty acid, sirolimus and shellac. One further preferred embodiment is a catheter balloon of a balloon catheter coated with α-linolenic acid (ALA C18:3) sirolimus and with shellac. This produces a coating which easily and quickly detaches from the catheter balloon and can effectively be transferred to the vessel wall.

Shellac is a natural resin produced from the glandular secretion of a number of species of lac-producing insects. Lac insects belong to the order of Hemiptera, superfamily Coccoidea such as Metatachardia, Laccifer, Tachordiella, and others, however, members of two families—Lacciferidae and Tachardimidae are more prominent in lac secretion. The one that is commercially cultured is *Kerria lacca*, which is also known by such synonyms as Laccifer lacca Ker, *Tachardia lacca*, and *Carteria lacca*. *Kerria lacca* is an Indian scale insect, which infests branches of numerous trees from the East Indies, such as *Butea frondos* Rosch, *Acacia arabica* Willd and *Ficus religiosa* Linn. Shellac is the only commercially used natural resin of animal origin and is quite different from all other natural resins. More recently, as a new awareness about the environments and the toxicity of chemical raw-material is noticeable everywhere, shellac or shellac modified resin are gaining importance due to their interesting and unique characteristics. Broken branches are sold as stick lac and, after grounding and washing with water to eliminate wood and red pigments (lac dye), seed lac is obtained. Purification of seed lac gives the more homogeneous product known as shellac.

Raw material shellac consists of 70-80% resin, 4-8% dye, 6-7% hard and high gloss finished wax, 3% water, up to 9% vegetable and animal impurities and aroma substances. Shellac resin is a complicated mixture of aliphatic (60%) and sesquiterpenoid acids (32%) and their esters. Sesquiterpenoid acids are jalaric and laccijalaric acids (structure I and II) and aliphatic acids are aleuritic (III) and butolic acid.

A possibility for chemical description of resin molecule is a structure model where in each case 4 molecules jalaric or laccijalaric acid and aleuritic acid are connected by ester bonding alternately.

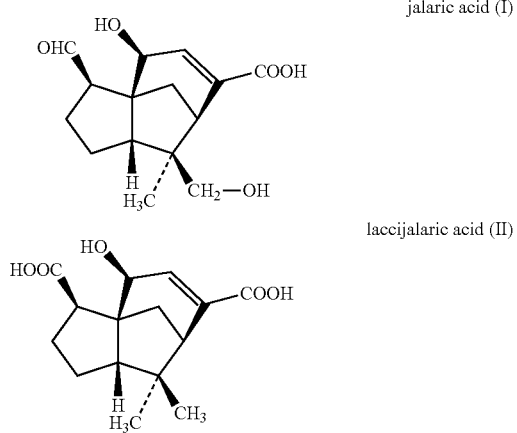

jalaric acid (I)

laccijalaric acid (II)

Its chemical composition is almost constant, although the amount of some components changes depending on the nature of host trees on which the insects grows. By Cannizzaro-type disproportionation under alkaline hydrolysis will be synthesized from these acids shellolic acid (IV) and deviate compounds. Purified shellac consists of two main components. These components are 9,10,16-trihydroxypalmitic acid (aleuritic acid) CAS [53-387-9] and shellolic acid (IV).

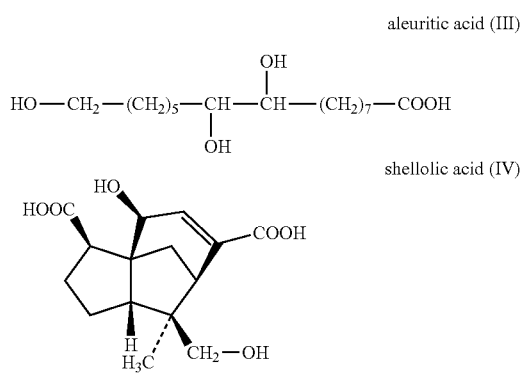

aleuritic acid (III)

shellolic acid (IV)

A modification with other natural or synthetic resins or co-polymerization with various monomers is possible to cross link shellac, modified shellac resins and shellac copolymers with urea, melamine, formaldehyde, isocyanides, other chemical processes like polymerization, hydroxylation, extrication, etc. are possible.

Followings are the commercial grades of shellac:

| | |
|---|---|
| Seedlac | Dewaxed Shellac |
| Hand Made Shellac | Dewaxed Bleached Shellac |
| Machine Made Shellac | Aleuritic Acid |

Major Properties of shellac are:
Shellac is a hard natural resin
Shellac has a good resistance against solvent
Shellac based on hydrocarbons
Shellac is non toxic
Shellac is thermoplastic
Shellac is physiologically harmless
Shellac is approved for various applications in the food industry.
Shellac is not UV-resistant
Shellac is soluble in lower alcohol's
Shellac has excellent dielectric properties high dielectric strength, low dielectric constant, good tracking resistance etc.
Shellac has a low melting point (65-85° C.).
Shellac is water soluble in water-alkaline solutions
Coatings do not change their electric properties under UV-radiation.
Shellac has excellent film forming properties.
Shellac has low thermal conductivity and a low coefficient of expansion forms smooth, high gloss films and surfaces.
Shellac coating has excellent adhesion to many coatings and can be polished.

A possibility for chemical description of resin molecule is a structure model where in each case 4 molecules jalaric or laccijalaric acid and aleuritic acid are connected by ester bonding alternately.

One embodiment of the present application refers to a catheter balloon wherein the further excipient, especially shellac, may be applied on the surface of the catheter balloon as a base coat or a top coat. Thereby an intermediate phase between the layer of the excipient and the layer containing sirolimus may exist. This intermediate layer is characterized in a mixture of both adjectant layer building a gradient. This means there is no clear cut where the underlying layer stops and the overlying layer starts but there is an area where one layer diffuses into the other layer.

Besides a catheter balloon coated with a combination of sirolimus, at least one fatty acid, oil or fat with shellac a catheter balloon coated with a combination of at least one fatty acid, such as omega fatty acids and especially omega-3 and omega-6 fatty acids, oil or fat with at least one polyethoxylated surfactant or at least one polyethoxylated emulsifier is also possible.

One preferred embodiment is therefore a catheter balloon of a balloon catheter coated with at least one fatty acid, such as omega fatty acids and especially omega-3 and omega-6 fatty acids, oil or fat, sirolimus and additionally with at least one polyethoxylated surfactant or at least one polyethoxylated emulsifier as a further excipient. Further one possible embodiment is a catheter balloon having a coating comprising at least one fatty acid, especially at least one free unsaturated fatty acid and more preferably free omega fatty acid, oil or fat, sirolimus, at least one polyethoxylated surfactant or at least one polyethoxylated emulsifier and shellac.

It is preferred that the at least one polyethoxylated surfactant or polyethoxylated emulsifier is selected from the group consisting of or comprising: polyethoxylated alcohols, polyethoxylated oils, polyethoxylated castor oil, polyethoxylated glycerol, polyethoxylated fatty acid esters, polyethoxylated phenols, polyethoxylated amines, polyethoxylated fatty alcohols. Among these surfactants or emulsifiers polyethoxylated castor oils are more preferred. Furthermore preferred are compounds which are produced by reacting higher saturated fatty alcohols with ethylene oxide, and particularly preferred are compounds which are made by reacting castor oil with ethylene oxide in a ration of 1:35, which means that it is prepared by reacting 35 moles of ethylene oxide with each mol of castor oil. Therefore one preferred embodiment is a catheter balloon of a balloon catheter coated with at least one fatty acid, such as omega fatty acids and especially omega-3 and omega-6 fatty acids, oil or fat, sirolimus and polyethoxylated castor oil.

The invention is further directed to a catheter balloon comprising a coating with at least one fatty acid, especially with at least one free unsaturated fatty acid and more preferably free omega fatty acid, oil or fat and sirolimus, wherein the coating comprises a top coat. The top coat is applied to protect the coating of sirolimus from premature dissolution and mechanical damage. Therefore the top coat is advantageous, because it protects the coating from a "wash off" effect and saves it for the instant release of active agent at the position of action. Preferred components of the top coating are polyacrylic acid and polyacrylates such as polymethylemethacrylate, polybutyl methacrylate, polyacrylamide, polyacrylonitriles, polyamides, polyether amides, polyethylenamine, polyimides, polycarbonates, polycarbourethanes, polyvinyl ketones, polyvinyl halogenides, polyvinyliden halogenides, polyvinyl ethers, polyvinyl aromates, polyvinyl esters, polyvinyl pyrollidones, polyvinyl alcohol, polyvinyl alcohol-polyethylene glycol graft copolymer, polyoxymethylenes, polyethylene, polypropylene, polytetrafluoroethylene, polyurethanes, polyolefine elastomers, polyisobutylenes, EPDM gums, fluorosilicones, carboxymethyl chitosane, polyethyl enterephthalate, polyvalerates, carboxymethyl cellulose, cellulose, rayon, rayontriacetates, cellulose nitrates, cellulose acetates, hydroxyethyl cellulose, cellulose butyrates, cellulose acetate-butyrates, ethylvinyl acetate copolymers, polysulfones, polyethersulfones, epoxy resins, ABS resins, EPDM gums, silicon prepolymers, silicones such as polysiloxanes, polyvinyl halogenes and copolymers, cellulose ethers, cellulose triacetates, chitosane, chitosane derivatives, natural polymers, polymerizable oils such as linseed oil and copolymers and/or mixtures thereof. More preferred is polyvinyl alcohol-polyethylene glycol graft copolymer and particularly preferred is a top coat of a polyvinyl alcohol-polyethylene glycol graft copolymer consisting of 75% polyvinyl alcohol units and 25% polyethylene glycol units which has preferably an average molecular weight within the range of 40,000 Daltons to 50,000 Daltons.

One preferred embodiment is therefore a catheter balloon of a balloon catheter coated with at least one fatty acid, especially with at least one free unsaturated fatty acid and more preferably free omega fatty acid, oil or fat, sirolimus, at least one polyethoxylated surfactant or at least one polyethoxylated emulsifier and a top coat. Preferably the balloon catheter coated with at least one fatty acid, oil or fat, sirolimus, at least one polyethoxylated surfactant or at least one polyethoxylated emulsifier has a top coat of polyvinyl alcohol-polyethylene glycol graft copolymer or shellac or a mixture thereof.

The term "base coat" as used herein refers to a layer of the coating of a catheter balloon which is immediately on the surface of the catheter balloon. This layer is a first layer which directly overlays the material of the catheter balloon as a priming coat which mainly increases the adherence of the sirolimus containing layer. The term "top layer" or "top coat" as used herein refers to a layer of the balloon coating free of any active agent which overlays the at least one sirolimus containing layer.

The term "uncoated" as used herein refers to a catheter balloon with a smooth or structured or roughened surface without any coating, i.e. the balloon surface does not comprise a pharmaceutically active agent and especially not sirolimus and no coating containing sirolimus.

Preferred is a catheter balloon having a coating with a proportion of sirolimus and the at least one fatty acid, especially free unsaturated fatty acid and more preferably free omega fatty acid, such as omega-3 and omega-6 fatty acid, oil or fat from 90% per weight of sirolimus to 10% per weight of the at least one fatty acid, especially free unsaturated fatty acid and more preferably free omega fatty acid, such as omega-3 and omega-6 fatty acid oil or fat to 10% per weight of sirolimus to 90% per weight of the at least one fatty acid, especially free unsaturated fatty acid and more preferably free omega fatty acid, such as omega-3 and omega-6 fatty acid, oil or fat. Especially preferred is a catheter balloon having a sirolimus containing layer with a proportion of sirolimus and the at least one fatty acid, especially free unsaturated fatty acid and more preferably free omega fatty acid, such as omega-3 and omega-6 fatty acid, oil or fat from 75% per weight of sirolimus to 25% per weight of the at least one fatty acid, especially free unsaturated fatty acid and more preferably free omega fatty acid, such as omega-3 and omega-6 fatty acid, oil or fat to 25% per weight of sirolimus to 75% per weight of the at least one fatty acid, especially free unsaturated fatty acid and more preferably free omega fatty acid, such as omega-3 and omega-6 fatty acid, oil or fat. Even more preferred is a catheter balloon having a sirolimus containing layer with a proportion of sirolimus and the at least one fatty acid, especially free unsaturated fatty acid and more preferably free omega fatty acid, such as omega-3 and omega-6 fatty acid, oil or fat from 70% per weight of sirolimus to 30% per weight of the at least one fatty acid, especially free unsaturated fatty acid and more preferably free omega fatty acid, such as omega-3 and omega-6 fatty acid, oil or fat to 60% per weight of sirolimus to 40% per weight of the at least one fatty acid, especially free unsaturated fatty acid and more preferably free omega fatty acid, such as omega-3 and omega-6 fatty acid, oil or fat.

The further excipients or carrier substances, like shellac and polyethoxylated surfactants or polyethoxylated emulsifiers, may be added in a weight ratio of up to 350% per weight relative to the at least one fatty acid, especially free unsaturated fatty acid and more preferably free omega fatty acid, such as omega-3 and omega-6 fatty acid oil or fat used, preferably up to 200% per weight, more preferably up to 1000% per weight relative to used fatty acids, especially free unsaturated fatty acid and more preferably free omega fatty acid, such as omega-3 and omega-6 fatty acid, oil or fat.

Also preferred is a catheter balloon with a coating whose molar ratio of active agent to the at least one fatty acid, oil or fat and a possible further excipient, like shellac and polyethoxylated surfactants or polyethoxylated emulsifiers, from 90% active agent to 10% matrix substances to 10% of active agent to 90% of matrix substances. Further preferred are mixtures of 1:5 to 5:1 and even more preferably from 1:2 to 2:1.

The use of at least one unsaturated fatty acid, especially free unsaturated fatty acids such as omega fatty acids and especially omega-3 and omega-6 fatty acids, is preferred over the use of an oil or a fat. Thus all ranges and values gives herein and all embodiments disclosed herein are especially in regard to free fatty acids and should be first of all interpreted in this way.

Thus especially preferred embodiments of the present invention relate to a coating of sirolimus together with at least one free fatty acid optionally together with shellac or with shellac as base coat and optionally together with a polyethoxylated surfactant or a polyethoxylated emulsifier and optionally with a top coat, preferably a top coat of polyvinyl alcohol-polyethylene glycol graft copolymer.

As omega fatty acids especially omega-3, omega-6 and omega-9 fatty acids are preferred and especially preferred are: α-Linolenic acid (ALA), Stearidonic acid (SDA), Eicosatrienoic acid (ETE), Eicosatetraenoic acid (ETA), Eicosapentaenoic acid (EPA), Linoleic acid (LA), Gamma-linolenic acid (GLA), Eicosadienoic acid, Dihomo-gamma-linolenic acid (DGLA), Arachidonic acid (AA), oleic acid, eicosenoic acid and mead acid.

Further one especially preferred embodiment of the present invention relates to a coating of sirolimus together with at least one free unsaturated fatty acid, with shellac and with a polyethoxylated surfactant or a polyethoxylated emulsifier and a top coat of polyvinyl alcohol-polyethylene glycol graft copolymer.

One preferred embodiment of the present invention relates also to a coating of sirolimus together with at least one free unsaturated fatty acid, with shellac and a top coat of polyvinyl alcohol-polyethylene glycol graft copolymer.

Especially preferred embodiments of the present invention relate to a coating of sirolimus together with at least one free omega fatty acid, especially omega-3, -6, -7 or -9 fatty acid and especially preferred omega-3 and omega-6 fatty acid optionally together with shellac or with shellac as base coat and optionally together with a polyethoxylated surfactant or a polyethoxylated emulsifier and optionally with a top coat, preferably a top coat of polyvinyl alcohol-polyethylene glycol graft copolymer.

One preferred embodiment of the present invention relates also to a coating of sirolimus together with at least one free unsaturated fatty acid, and even more preferably free fatty acids having 18-22 C-atoms, with shellac optionally together with a polyethoxylated surfactant or a polyethoxylated emulsifier and a top coat of polyvinyl alcohol-polyethylene glycol graft copolymer.

One embodiment of the invention is a catheter balloon coated with sirolimus, together with at least one free unsaturated fatty acid and a top coat preferably consisting of a polyvinyl alcohol-polyethylene glycol graft copolymer. Preferred embodiments of the invention have a coating comprising sirolimus, together with at least one free omega fatty acid, especially omega-3 and omega-6 fatty acid and at least one polyethoxylated surfactant or at least one polyethoxylated emulsifier. Optionally a top coat, preferably a top coat of polyvinyl alcohol-polyethylene glycol graft copolymer is applied, too.

Also preferred is a catheter balloon with a coating comprising sirolimus, together with α-linolenic acid, with shellac and with a polyethoxylated surfactant or a polyethoxylated emulsifier and optionally a top coat of polyvinyl alcohol-polyethylene glycol graft copolymer.

A particular preferred embodiment of the present invention is a catheter balloon with a coating comprising sirolimus embedded in α-linolenic acid optionally with a polyethoxylated surfactant or a polyethoxylated emulsifier, shellac as base coat and a top coat of polyvinyl alcohol-polyethylene glycol graft copolymer.

Concerning all embodiments disclosed herein the use of free fatty acids, i.e. the use of protonated fatty acids and not of fatty acid salts (deprotonated), fatty acid esters or fatty acid amides or any other fatty acid derivatives is preferred. Moreover it is preferred that these free fatty acids contain or have between 1 and 5 double bonds and contain or have between 10 and 30 carbon atoms, more preferably between 12 and 28, still more preferably between 14 and 26, still more preferably between 16 and 24, and most preferably between 18 and 22 carbon atoms. Preferably these carbon atoms form a linear unbranched carbon chain. The double bonds in the fatty acids preferably have Z conformation.

According to the invention, a catheter balloon coated with at least one fatty acid, especially free unsaturated fatty acid and more preferably free omega fatty acid, oil or fat and sirolimus, may be prepared by one of the following methods, preferably under sterile conditions. First, the at least one fatty acid, especially free unsaturated fatty acid and more preferably free omega fatty acid, oil or fat and sirolimus are mixed with a solvent. Optionally a further excipient like shellac and the at least one polyethoxylated surfactant or at least one polyethoxylated emulsifier may also be solved in said coating solution. The solvent is selected from the group comprising or consisting of acetone, ethanol, methanol, dimethyl sulfoxide, terahydrofuran, chloroform, methylene chloride, ethyl acetate, water and/or mixtures of the above mentioned solvents. The at least one fatty acid, especially free unsaturated fatty acid and more preferably free omega-3, -6, -7 or -9 fatty acid, oil or fat and sirolimus in the solvent or in a solvent mixture may be applied to the surface of the catheter balloon by any common method like dipping, spraying, brushing or pipetting. Then the solvent or the solvent mixture should be removed by evaporation at room temperature or by drying in an oven and the coated balloon catheter may be folded.

One method for producing a coating of catheter balloons according to the invention is, characterized in that the following steps are contained:

a) mixing the at least one fatty acid, such as omega fatty acid and especially omega-3 and omega-6 fatty acid, oil or fat and sirolimus with a solvent and b) deposition of the mixture of the at least one fatty acid, such as omega fatty acid and especially omega-3 and omega-6 fatty acid, oil or fat and sirolimus in the solvent via dipping, spraying, spreading or pipetting method, and c) drying the coating.

The present invention further comprises a method for producing of coating of catheter balloons according to the invention, characterized by the following steps:

a) mixing the at least one fatty acid, such as omega fatty acid and especially omega-3 and omega-6 fatty acid, oil or fat, sirolimus and the at least one additive, like shellac or polyethoxylated castor oil with a solvent and b) deposition of the mixture of the at least one fatty acid, such as omega fatty acid and especially omega-3 and omega-6 fatty acid, oil or fat, sirolimus and the at least one additive, like shellac or polyethoxylated castor oil, in the solvent via dipping, spraying, spreading or pipetting method, The following step d) may be follow the above described methods d) folding of the catheter balloon.

Step d) is particular important if the catheter balloon is coated in a dilatated or partly dilatated state.

Further step e) may be follow step d) or step c) of the above described methods.

e) crimping a coated or uncoated stent on the folded catheter balloon.

In another preferred embodiment, firstly a coating of shellac is applied to the catheter balloon and subsequently on this base coat or first layer sirolimus is applied as a second layer or as a further coat. Thereby the catheter balloon coated with shellac is dipped in a solution of at least one fatty acid, such as omega fatty acid and especially omega-3 and omega-6 fatty acid, oil or fat and sirolimus or the solution comprising the at least one fatty acid, such as omega fatty acid and especially omega-3 and omega-6 fatty acid, oil or fat and sirolimus is sprayed or pipetted on the coating of shellac. It is also possible to coat first the at least one fatty acid, especially free unsaturated fatty acid and more preferably free omega fatty acid, such as omega-3 and omega-6 fatty acid, oil or fat optionally in combination with shellac and/or the one polyethoxylated surfactant or at least one polyethoxylated emulsifier and in a second step apply sirolimus on the balloon. The layer of the at least one fatty acid, oil or fat and optionally shellac and/or the one polyethoxylated surfactant or at least one polyethoxylated emulsifier absorbs the coating solution containing sirolimus at least partially.

The catheter balloon can be in a folded, partially unfolded or fully expanded state during the coating process. Thereby it is possible to coat the complete surface of the catheter balloon or only the folds of the catheter balloon or other special structures of or on the balloon surface as well as a surface of a stent crimped on the catheter balloon entirely or partially with the at least one fatty acid, especially free unsaturated fatty acid and more preferably free omega fatty acid, such as omega-3 and omega-6 fatty acid, oil or fat and sirolimus.

During a further step a stent may be crimped on the folded catheter balloon, wherein the stent can be uncoated or coated with at least one active agent or a combination of an active agent with a matrix substance or a mixture of matrix substances. The stent is suitable to reduce or prevent restenosis. The at least one active agent which may be coated on the stent can be an anti-inflammatory, cystostatic, cytotoxic, antiproliferative, anti-microtubuli, anti-angiogenic anti-restenotic, antifungicide, antineoplastic, antimigrative, athrombogenic or antithrombogenic substances and can be selected from the group as described above for a second active agent on the catheter balloon.

Catheter balloons according to the invention, optionally together with an uncoated or active agent-coated stent crimped on, are further characterized in that the applied coating on the catheter balloon, and optionally on the stent, provides a sufficient lubricity, so that no need for additional lubricants exists.

The catheter balloons according to invention solve both the problem of acute thrombosis and the problem of neointima hyperplasia after angioplasty and optionally stent implantation. In addition the catheter balloons according to invention are especially well suited, because of their coating, whether as mono-layer or as poly-layer system, for a short-term release of sirolimus. Due to this capability of short-term sirolimus release in a required amount the inventively coated catheter balloons reduce the risk of inflammation and of restenosis.

EXAMPLES

Example 1

Coating with Sirolimus and α-Linolenic Acid

Figure 1:
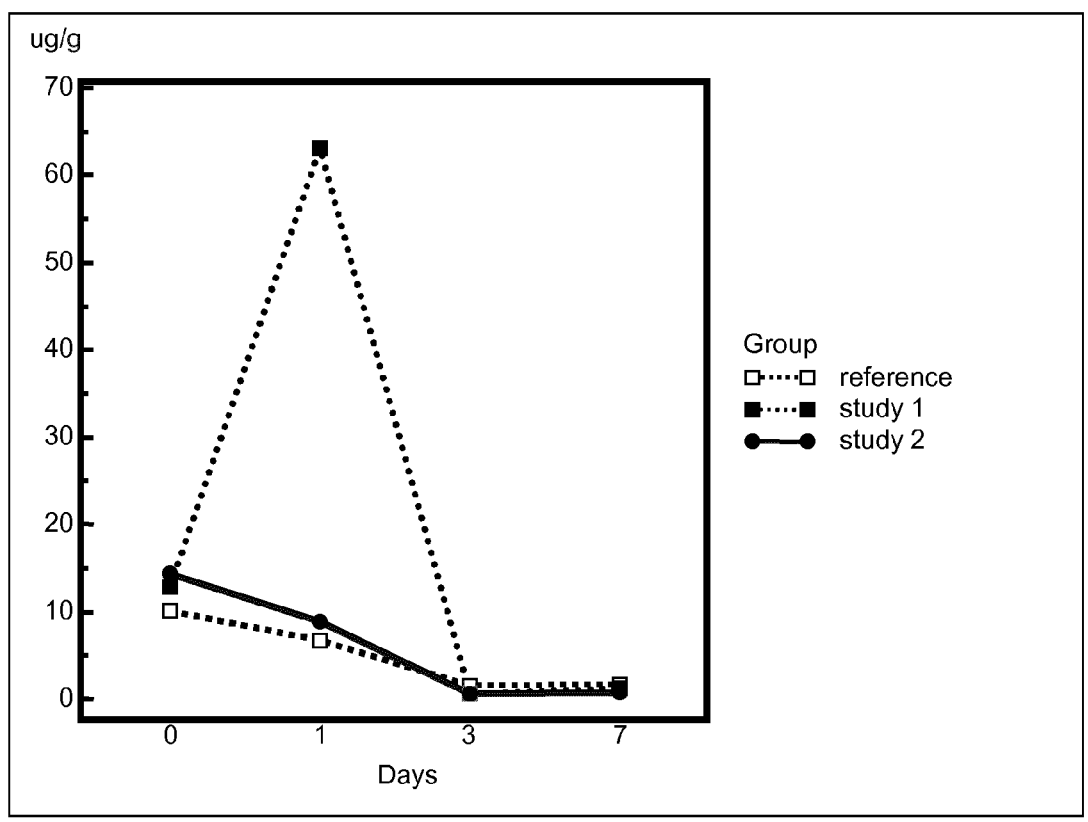
FIG. 1: Intramural Paclitaxel and Sirolimus median concentration [µg/g]
Figure 2:
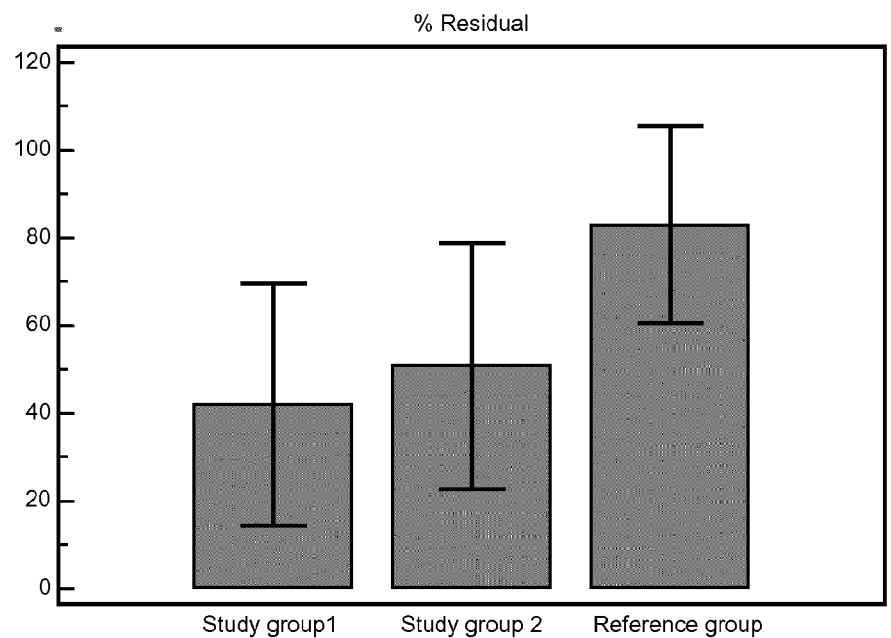
FIG. 2: Residuals of Paclitaxel and Sirolimus on catheter balloons after balloon angioplasty in pigs (example 16)—shown is the average residual in percentage of total loading dose
Figure 3:
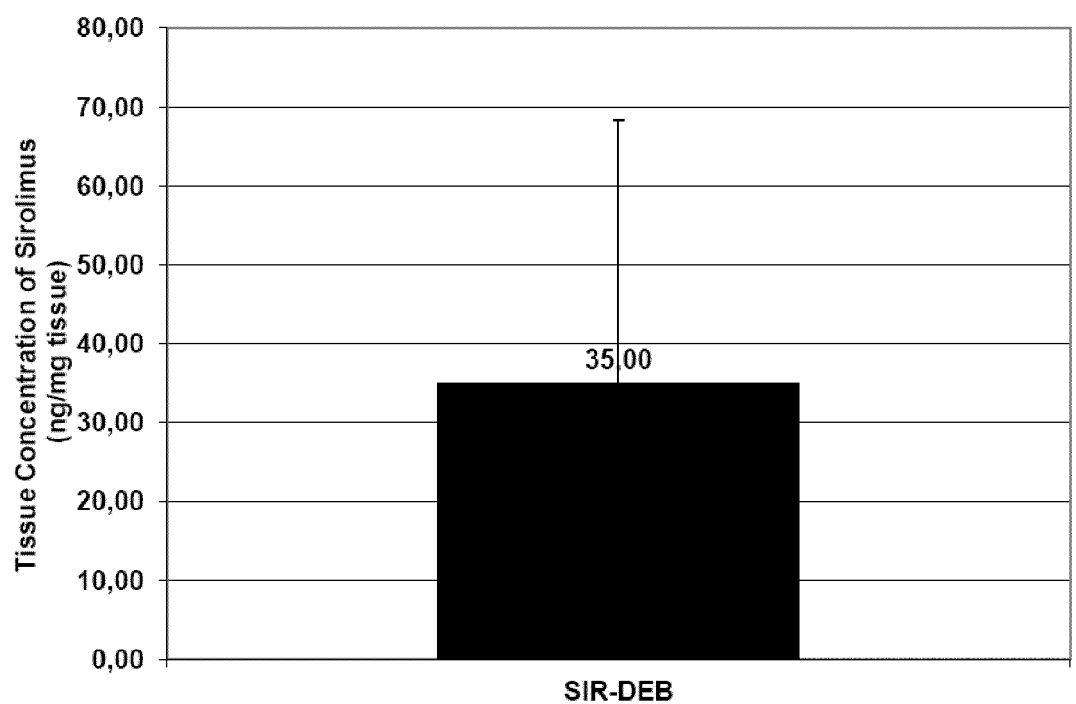
FIG. 3: Mean Tissue sirolimus concentration [ng/mg] 1 hour after dilatation of the balloon of example 17.

Sirolimus is solved in DMSO containing ca. 10 vol. % of water. α-Linolenic acid and shellac are added to this solution and the catheter balloon is coated several times with this solution by using the spraying method (e.g. EVOLUTION spraying pistol from Harder & Steenbeck) and dried after the coating.

Example 2

Coating of the Folds of a Catheter Balloon Only

A mixture of α-linolenic acid, polyethoxylated castor oil (2:1) and sirolimus in ethanol and water is prepared, filled into a pipette and squirted by means of the pipette under the folds of a multifold balloon. After drying a powdery coating of the fold interspaces results, which is easily detached on dilating the balloon.

Example 3

Coating of a Catheter Balloon with Shellac and α-Linolenic Acid (1:3)

A mixture of α-linolenic acid and shellac (3:1) in ethanol and water is prepared, filled into a pipette and squirted by means of the pipette on the complete surface of a catheter balloon. Afterwards the catheter balloon was dried for 24 h at room temperature.

Example 4

Coating of a Catheter Balloon Sirolimus and Stearidonic Acid

A common balloon catheter with an expandable catheter balloon, which may be used for vessel dilatation, is removed from fat in the ultrasonic bath for 15 minutes with acetone and ethanol and dried at 100° C. in the drying oven until acetone and ethanol are evaporated. Subsequently the catheter balloon is washed with demineralized for 12 hours. 10 mg of Sirolimus are solved in 1 mL of ethanolic solution of stearidonic acid (Cayman Chemical). The mixture is sprayed with an airbrush spraying pistol from a distance of 5.8 cm on a rotating 18 mm LVM balloon catheter. Afterwards the coated balloon was dried for 24 h at 30° C. Optionally the coated catheter balloon may be folded and an uncoated or active agent-coated stent may be crimped on the folded catheter balloon.

Example 5

Adding of Sirolimus to a Coated Balloon in the Dipping Method Using Sterile Conditions The catheter balloon coated according to example 3 was dipped into a solution of 300 µg of sirolimus in 1 ml of ethanol and allowed to swell. After accomplishing the swelling process of the coating the catheter balloon was pulled out of the solution, air dried for 120 minutes at room temperature and folded. Optionally an uncoated or active agent-coated stent may be crimped on the folded catheter balloon.

Example 6

Biocompatible Coating of a Catheter Balloon with Linseed Oil, Sirolimus and Paclitaxel A common balloon catheter with an expandable catheter balloon, which may be used for vessel dilatation, is removed from fat in the ultrasonic bath for 15 minutes with acetone and ethanol and dried at 100° C. in the drying oven until acetone and ethanol are evaporated. Subsequently the balloon catheter was washed with demineralized water for 14 hours. Linseed oil, sirolimus and paclitaxel (80:10:10 percent by weight) are dissolved in the mixture ratio of 1:1 in chloroform after the resulting volume has been measured. Subsequently the mixture is sprayed on the balloon surface of the continuously rotating balloon catheter. After evaporation of the chloroform in the soft air stream the balloon catheter is dried at 80° C. Optionally the coated catheter balloon may be folded and an uncoated or active agent-coated stent may be crimped on the folded catheter balloon.

Example 7

Biocompatible Coating of a Catheter Balloon with an Ethanolic Linseed Oil Spraying Solution with 0.25 Percent by Weight of Linseed Oil A common balloon catheter with an expandable catheter balloon, which may be used for vessel dilatation, is removed from fat in the ultrasonic bath for 15 minutes with acetone and ethanol and dried at 100° C. in the drying oven. Subsequently the balloon catheter was washed with demineralized water for 14 hours. A spraying solution of linseed oil, sirolimus and ethanol is prepared and continuously sprayed with a spraying pistol on the balloon surface of the balloon catheter rotating around its axis. The balloon catheter with the coated balloon is dried for 13 hours at 70° C. The average coating mass is 0.20 mg±0.04 mg. Optionally the coated catheter balloon may be folded and an uncoated or active agent-coated stent may be crimped on the folded catheter balloon.

Example 8

Biocompatible Coating of a Catheter Balloon with an Ethanol Spraying Solution of Gamma-Linolenic Acid, Polyethoxylated Stearic Acid and Sirolimus After cleaning of the catheter balloons as already described in the example 6 an ethanol spraying solution is prepared which contains 0.25% gamma-linolenic acid and 0.1% polyethoxylated stearic acid. Subsequently, sirolimus is solved in this ethanolic solution. The ethanolic solution is continuously sprayed with a spraying pistol on the balloon surface of a rotating balloon catheter, which is suitable for vessel dilatation. Then the balloon catheter is dried for 15 hours at 70° C. The average coating mass is 0.3 mg±0.06 mg. Optionally the coated catheter balloon may be folded and an uncoated or active agent-coated stent may be crimped on the folded catheter balloon.

Example 9

Coating of a Catheter Balloon with Sirolimus, α-Linolenic Acid and Shellac in a Two Layer System with Addition of a Top Coat The balloon of a balloon catheter is cleaned as described in the example 6. After cleaning a first layer of 0.25% by weight of sirolimus, α-linolenic acid and shellac dissolved in DMSO is continuously sprayed on the balloon surface of a rotating balloon catheter. This layer is dried for 4.5 hours at room temperature. Subsequently the second layer of an ethanol solution with 0.1% polyvinyl alcohol-polyethylene glycol graft copolymer is sprayed on this first layer. The balloon catheter with the coated balloon is dried over 24 hours at 50° C. The average coating mass is determined to be 0.25 mg±0.02 mg. Optionally the coated catheter balloon may be folded and an uncoated or active agent-coated stent may be crimped on the folded catheter balloon.

Example 10

Coating of a Catheter Balloon with Sirolimus, α-Linolenic Acid and Shellac in a Two Layer System with Addition of a Base Coat The balloon of a balloon catheter is cleaned as described in the example 6. After cleaning of the balloon a first layer of 0.3% by weight of shellac dissolved in ethanol is sprayed on the balloon surface of a balloon catheter. This layer is dried at room temperature over 12.5 hours. Subsequently, the second layer of a DMSO solution with 0.25% by weight of sirolimus, α-linolenic acid and shellac is sprayed on the base coat of shellac. After drying over 20 hours at 30° C. the coating mass is determined to be 0.42 mg±0.07 mg. Optionally the coated catheter balloon may be folded and an uncoated or active agent-coated stent may be crimped on the folded catheter balloon.

Example 11

Coating of a Catheter Balloon with Linseed Oil and α-Linolenic Acid

A common balloon catheter with an expandable catheter balloon, which may be used for vessel dilatation, is removed from fat in the ultrasonic bath for 15 minutes with acetone and ethanol and dried at 100° C. in the drying oven until acetone and ethanol are evaporated. Then a mixture of 0.20% per weight linseed oil and 0.5% per weight α-linolenic acid solved in ethanol is prepared. This mixture is continuously sprayed on the balloon surface of a rotating balloon catheter. A drying step takes place over 14 hours at 70° C. The average coating mass is 0.3 mg±0.04 mg. Optionally the coated catheter balloon may be folded and an uncoated or active agent-coated stent may be crimped on the folded catheter balloon.

Example 12

Study of Restenosis Inhibition by Sirolimus after Angioplasty and Stent Implantation in the Coronary Arteries of Pigs The balloon surfaces of balloon catheters suitable for vessel dilatation has been coated as described in table 9. After drying a common, uncoated metal stent was crimped on each balloon catheter. The balloon catheter together with the stents were sterilized packed into protective covers and stored until usage at room temperature.

For stimulation of restenosis caused by tissue hyperplasia coronary vessels (LAD and LCx) of 50 pigs were stretched using a balloon catheter. The animals used were female and castrated male pigs of Yorkshire breed. The weight of the animals at the beginning of the experiment ranged between 24 to 35 kg; the age of the animal was about 12 to 15 weeks. The group size was five animals each.

The vessel dilatation of LAD and LCx using balloon dilatation was performed for 30 seconds in the ratio balloon/artery in the range of 1.2 to 1 and 1.3 to 1 and was repeated once. Thereafter, the crimped stents were implanted into the vessel wall so that a stent was implanted in LAD and LCx of each animal. For the balloon dilatation balloons coated according to the invention were used. Table 9 shows an overview of the used coatings and coating methods.

TABLE 9

Overview of coatings and stent implantation

| Group (n = 5) | Balloon surface coated with | Stent implantation |
| --- | --- | --- |
| 1 | No coating | 1 × LAD, 1 × $LC_x$ |
| 2 | Linseed oil + PVP | 1 × LAD, 1 × $LC_x$ |
| 3 | α-linoleic acid + PVP | 1 × LAD, 1 × $LC_x$ |
| 4 | Linseed oil + sirolimus | 1 × LAD, 1 × $LC_x$ |
| 5 | Linseed oil + PVP + sirolimus | 1 × LAD, 1 × $LC_x$ |
| 6 | Linseed oil + PVP + sirolimus (PVP as a top coat) | 1 × LAD, 1 × $LC_x$ |
| 7 | Linseed oil + α-linoleic acid | 1 × LAD, 1 × $LC_x$ |
| 8 | α-linoleic acid + sirolimus | 1 × LAD, 1 × $LC_x$ |
| 9 | α-linoleic acid + sirolimus + PVP (PVP as a top coat) | 1 × LAD, 1 × $LC_x$ |

After 28 days angiography was carried out at the LAD and LCx of the animals. Stenosis grad gives the percent reduction of the lumen diameter in the area of the stent to the lumen diameter immediately after implantation of the stent. Values are expressed as mean values±standard deviation. Differences compared to group 1 which was treated with balloon catheters with uncoated balloons were considered significant at a value of P<0.05. The results are shown in Table 10.

TABLE 10

Results of angiography after 28 days

| Group (n = 5) | Surface coating | Degree of stenosis % [mean value ± standard deviation] (P-value in comparison to group 1) |
| --- | --- | --- |
| 1 | No coating | 44.6 ± 17.1 |
| 2 | Linseed oil + PVP | 38.8 ± 19.6 (P = 0.490) |
| 3 | α-linoleic acid + PVP | 37.2 ± 18.0 (P = 0.358) |
| 4 | Linseed oil + sirolimus | 23.3 ± 19.4 (P = 0.018) |
| 5 | Linseed oil + PVP + sirolimus | 17.2 ± 19.3 (P = 0.004) |
| 6 | Linseed oil + PVP + sirolimus (PVP as a top coat) | 13.7 ± 18.1 (P = 0.001) |
| 7 | Linseed oil + α-linoleic acid | 29.9 ± 24.3 (P = 0.135) |
| 8 | α-linoleic acid + sirolimus | 10.7 ± 15.1 (P = 0.011) |
| 9 | α-linoleic acid + sirolimus + PVP (PVP as a top coat) | 9.8 ± 13.5 (P = 0.006) |

Example 13

Determination of the Degree of Inflammation in the Treated Tissue Area after 28 Days After angiography, the animals of Example 12 were euthanized and coronary tissue samples were taken for histology. The degree of inflammation was evaluated using the following classification:

0 media or intima shows no inflammation o rare interspersed with small amounts of inflammatory cells
  1 weak infiltration or moderate inflammatory lesions within less of 25% of the vessel area in the media or intima
  2 moderate infiltration or notable inflammatory lesions between 25% to 50% of the vessel area in the media or intima
  3 strong infiltration or notable inflammatory lesions within more than 50% of the vessel area in the media or intima
  4 granulomatous inflammatory reaction in any layer of the artery The results of determination the degree of inflammation after 28 days are shown by table 11. Values represent mean values±standard deviation. Differences to group 1 which was treated with balloon catheters with uncoated balloons were considered significant at a value of P<0.05. All investigated coatings resulted in no significant increase in levels of inflammation after 28 days.

TABLE 11

Degree of inflammation after 28 days

| Group (n = 5) | Surface coating | Degree of inflammation [mean value ± standard deviation] (P-value in comparison to group 1) |
| --- | --- | --- |
| 1 | No coating | 0.40 ± 0.80 |
| 2 | Linseed oil + PVP | 0.81 ± 0.79 (P = 0.2369) |
| 3 | α-linoleic acid + PVP | 0.80 ± 0.63 (P = 0.2301) |
| 4 | Linseed oil + sirolimus | 0.70 ± 1.06 (P = 0.4842) |
| 5 | Linseed oil + PVP + sirolimus | 0.70 ± 0.82 (P = 0.4185) |
| 6 | Linseed oil I + PVP + sirolimus (PVP as a top coat) | 0.90 ± 1.10 (P = 0.2602) |
| 7 | Linseed oil + α-linoleic acid | 0.60 ± 0.94 (P = 0.6146) |
| 8 | α-linoleic acid + sirolimus | 0.95 ± 0.80 (P = 0.2301) |
| 9 | α-linoleic acid + sirolimus + PVP; (PVP as a top coat) | 0.8 ± 1.05 (P = 0.006) |

Example 14

Coating of a Folded Balloon with Oleic Acid and Sirolimus Using Pipetting Method A common balloon catheter with an expandable, folded balloon, which may be used for vessel dilatation, is removed from fat in the ultrasonic bath for 15 minutes with acetone and ethanol and dried at 100° C. in the drying oven until acetone and ethanol are evaporated. Subsequently, the folded balloon is washed with demineralized water over 12 hours. A mixture of 85% per weight oleic acid and 15% per weight sirolimus is produced and the same volume ethanol is added to the resulting mixture. The folded balloon is tethered in a horizontal position on the rotatable axis so that the fold to be filled is always lying upside. Thus step by step each fold is filled with the coating solution from the beginning to the end of the fold by means of a teflon cannula as enlargement of a needle syringe. Subsequently the coated balloon catheter is dried over night by room temperature until the solvent is evaporated completely. Then a coated or uncoated stent may be crimped on, if desired.

Example 15

Coating of a Folded Balloon with Oleic Acid/Shellac and Sirolimus Using Pipetting Method The folded balloon of a balloon catheter is cleaned and coated as described in example 13. But the coating solution is produced using 40% per weight oleic acid, 40% per weight shellac and 20% per weight sirolimus. The same volume ethanol is added to the resulting mixture.

Example 16

Pharmacokinetic Evaluation of Sirolimus Eluting, Hydrophilically Coated Balloons in an Overstretch Model of Porcine Coronary Arteries 1—Material and Methods Eight Polish Domestic pigs of 35-42 kg body weight were included in the study in which 24 sirolimus and paclitaxel eluting balloons (, cf. above) were deployed. Procedures were carried out in the Center for Cardiovascular Research of American Heart of Poland. The appropriate approval of regional Bioethical Committee was obtained. The three coronary arteries (LAD, LCx, RCA) of each animal were randomly assigned in 1:1:1 ratio to either study group or reference group. All animals received dual antiplatelet therapy consisting of oral acetylsalicylic acid (325 mg) and clopidogrel (300 mg initial dose and 75 mg subsequently) starting three days prior to intervention and continuing until sacrifice. After anesthesia induction with propofol the animals were intubated and supported with mechanical ventilation. A propofol continuous infusion was started to maintain a surgical plane of anesthesia. Subsequently, an arterial sheath was introduced to the left or right femoral artery utilizing percutaneous Seldinger technique. An initial bolus of heparin (~400 U/kg) was administered and activated clotting time (ACT) was measured every 30 minutes to maintain ACT time of at least 300 seconds. Coronary angiograms were performed after administration of intracoronary nitroglycerin (200 µg). The selection of the target site was made based on visual assessment of anatomy and quantitative coronary angiography (QCA) analysis. These sites were chosen for the avoidance of side branches and segments with tapering greater than 10% to ensure uniform interaction of the stent coating with the arterial wall. The balloon was then inflated at a steady rate to a pressure sufficient to achieve a balloon to artery ratio of 1.2:1 (acceptable range of 1.15:1 to 1.25:1). At pre-determined time points the animals were euthanized. The hearts were harvested as quickly as possible after euthanasia, using precautions to avoid damage to the study vessels. The hearts were examined for abnormal findings and were labeled with the animal identification number, protocol number and date of collection. The hearts were flushed with normal saline until cleared of blood and then pressure-perfusion fixed at 80-100 mmHg with 10% neutral buffered formalin (NBF). Samples of abnormal tissues were collected and undergo immersion fixation with 10% NBF. All study vessel segment were labeled with the animal identification number, protocol number, tissue types and date of collection. All tissues were placed in containers and frozen in dry ice in −68° C. and sent to the HPLC test site. The heart for each animal was placed in its own separate container.

Sirolimus and Paclitaxel Eluting Balloon Catheter Characteristics:

Three studied catheters with the following coatings were evaluated:
1. study group 1: 3.0 µg/mm$^2$ Sirolimus+Shellolic Acid++ 0.5 µg/mm$^2$ α-linolenic acid coated balloon
2. study group 2: 3.0 µg/mm$^2$ Sirolimus+Shellolic Acid coated balloon
3. reference group: =3.0 µg/mm$^2$ Paclitaxel+3.0 µg/mm$^2$ Shellac coated balloon All used balloons were 3.0 or 3.5 mm in diameter and 20 mm in length.

Qualitative Coronary Angiography

The Quantitative Coronary Angiography (QCA) analysis was performed by blinded operator with the off line QAngioX 7.2, MEDIS Software and angiograms were recorded in DICOM format. Two contralateral projections were chosen for balloon deployment site assessment.

HPLC Analysis (Appendix 1)

The paclitaxel or sirolimus concentration of plasma, LAD, LCx and RCA was measured by high-performance liquid chromatography (AnaKat Institut for Biotechnologie GmbH, Berlin, Germany, analysis blinded to sample origin). Briefly, after thawing, the tissues were weighed at ambient temperature and, depending on the weights; different volumes of ethanol were added to the samples (sufficient ethanol to cover the tissue completely). The samples were then treated with ultrasound for 40 minutes. About 200 ml samples were centrifuged. A calibration line was produced in the range between 50 and 5000 ng/ml. The samples for the calibration line were prepared by dilution of a stock solution with a concentration of 1000 mg/ml. Aliquots of all samples (samples from tissue and calibration line) were transferred into autosampler vials and the same volume of 0.1% formic acid was added. The flow rate of the high performance liquid chromatography system was 0.2 ml/min through a column of ODS Hypersil (ThermoElectron Corporation, Thermo Scientific, Waltham, Mass., USA), particle size 5 m, pore size 120 A°. The isocratic mobile phase consisted of 70% methanol containing formic acid (0.1%). Paclitaxel was detected by mass spectrometry in multiple reaction-monitoring mode with a transition of paclitaxel from 854 to 105 AMU. The tissue paclitaxel/sirolimus concentration was expressed in µg/g.

Follow-Up

The animals were scheduled for 1 hour, 1, 3 and 7 days (2 pigs per each time period) according to table 12.

TABLE 12 scheme of balloon angioplasty

| Animal no. | Follow up (days) | Group | Artery |
|---|---|---|---|
| 1 | 7 | Study group_1 | lad |
| 1 | 7 | Study group_2 | lcx |
| 1 | 7 | Reference group | rca |
| 2 | 7 | Reference group | lcx |
| 2 | 7 | Study group_2 | lad |
| 2 | 7 | Study group_1 | rca |
| 3 | 3 | Study group_2 | rca |
| 3 | 3 | Study group_1 | lcx |
| 3 | 3 | Reference group | lad |
| 4 | 3 | Study group_1 | lcx |
| 4 | 3 | Reference group | lad |

TABLE 12-continued scheme of balloon angioplasty

| Animal no. | Follow up (days) | Group | Artery |
|---|---|---|---|
| 4 | 3 | Study group_2 | rca |
| 5 | 1 | Study group_2 | rca |
| 5 | 1 | Study group_1 | lad |
| 5 | 1 | Reference group | lcx |
| 6 | 1 | Study group_2 | lcx |
| 6 | 1 | Study group_1 | lad |
| 6 | 1 | Reference group | rca |
| 7 | 0 | Study group_1 | rca |
| 7 | 0 | Study group_2 | lcx |
| 7 | 0 | Reference group | lad |
| 8 | 0 | Reference group | lcx |
| 8 | 0 | Study group_2 | lad |
| 8 | 0 | Study group_1 | rca |

Statistical Analysis:

Results are expressed as mean±standard deviation (SD). Normal distribution of variables was verified by Kolmogorov-Smirnov test. The variance uniformity was verified with the use of Levene test. Angiographic and HPLC analysis data were analyzed using ANOVA tests. In case of skewed distribution or non-uniformity of variance a non-parametric Kruskal-Wallis and U Mann-Whitney tests were used. The p-value<0.05 was considered statistically significant. Statistical analysis was performed utilizing Statistica 7.0 StatSoft Software.

Results

Pre-Operative Procedures

After an overnight fast, the animals were pre-anesthetized with a mixture based on body weight. These active agents include: Atropine (1 mg/20 kg sc.), Ketamine (1 ml/10 kg im) and Xylazine (1 ml/10 kg im). The injection was given intramuscularly (im) in either the neck or rear muscle quadrant by a qualified animal technologist. The animal was transferred to the preparation room, where an intravenous line was placed in the auricular marginal vein, and intravenous fluids (lactated ringers or 0.9% saline) were administered throughout the procedure. Anti-arrhythmics were added to these IV fluids (Lidocaine 200 mg/liter, Metoprolol 5 mg/liter). After the animal reached an adequate anesthetic plane (with a propofol bolus) it was intubated with an appropriate size endotracheal tube, which was tied into place and the cuff inflated to prevent leakage. The animal was then transferred to the catheter lab, placed on the table and attached to the anesthesia and ventilator unit.

Procedures

In total 24 balloons were deployed, eight Study group 1 (five 3.5 mm and three 3.0 mm), eight Study group 2 (three 3.5 and five 3.0 mm) and 8 Reference group as shown in Table 12. Each of them was inspected before delivery. No signs of structure abnormality were noticed. The coating was not visible. Balloons were easily introduced into the selected arterial segment through femoral artery access and successfully deployed in the desired segment after live QCA guidance to ensure balloon/artery ratio 1.2:1. All tested balloons were inflated for 60 s. Due to overstretch in one case a dissection, limiting blood flow occurred. This required a stent implantation proximally to the tested site.

Baseline Vessel and Balloon Deployment Characteristics:

There were no differences in the baseline QCA results such as vessels baseline reference diameter, minimal lumen diameter, balloon diameter and stent to artery ratio in the whole group as well as within each time period between the studied groups (Table 13). The average overstretch was 110-120% and was reproducible among groups. All tested balloons stayed in circulation for 3 minutes±20 seconds

TABLE 13

Baseline QCA vessel characteristics

| [mm] All | RD Average ± SD | MLD Average ± SD | Balloon Average ± SD | S-2-A Average ± SD |
|---|---|---|---|---|
| Total n = 24 | | | | |
| STUDY GROUP 1 | 2.72 ± 0.36 | 2.93 ± 0.39 | 3.07 ± 0.25 | 1.14 ± 0.13 |
| STUDY GROUP 2 | 2.71 ± 0.35 | 2.92 ± 0.33 | 3.00 ± 0.27 | 1.10 ± 0.09 |
| REFERENCE GROUP | 2.60 ± 0.40 | 2.78 ± 0.38 | 2.96 ± 0.28 | 1.15 ± 0.08 |
| P ANOVA | ns | ns | ns | ns |
| 1 hour (0) n = 6 | | | | |
| STUDY GROUP 1 | 2.88 ± 0.45 | 3.01 ± 0.42 | 3.11 ± 0.21 | 1.10 ± 0.24 |
| STUDY GROUP 2 | 2.44 ± 0.41 | 2.64 ± 0.51 | 2.88 ± 0.20 | 1.19 ± 0.11 |
| REFERENCE GROUP | 2.81 ± 0.53 | 2.97 ± 0.48 | 3.11 ± 0.35 | 1.12 ± 0.09 |
| P ANOVA | ns | ns | ns | Ns |
| 1 day n = 6 | | | | |
| STUDY GROUP 1 | 2.50 ± 0.15 | 2.69 ± 0.25 | 3.05 ± 0.24 | 1.23 ± 0.02 |
| STUDY GROUP 2 | 3.06 ± 0.35 | 3.23 ± 0.28 | 3.28 ± 0.27 | 1.08 ± 0.04 |
| REFERENCE GROUP | 2.27 ± 0.21 | 2.43 ± 0.24 | 2.81 ± 0.25 | 1.24 ± 0.00 |
| P ANOVA | ns | ns | ns | ns |
| 3 days n = 6 | | | | |
| STUDY GROUP 1 | 2.64 ± 0.71 | 2.85 ± 0.74 | 2.99 ± 0.43 | 1.15 ± 0.14 |
| STUDY GROUP 2 | 2.54 ± 0.18 | 2.95 ± 0.05 | 3.00 ± 0.00 | 1.12 ± 0.00 |
| REFERENCE GROUP | 2.72 ± 0.31 | 2.89 ± 0.20 | 3.03 ± 0.38 | 1.11 ± 0.01 |
| P ANOVA | ns | ns | ns | Ns |
| 7 days n = 6 | | | | |
| STUDY GROUP 1 | 2.86 ± 0.02 | 3.19 ± 0.08 | 3.15 ± 0.36 | 1.10 ± 0.11 |
| STUDY GROUP 2 | 2.79 ± 0.28 | 2.85 ± 0.27 | 2.84 ± 0.30 | 1.02 ± 0.00 |

TABLE 13-continued

Baseline QCA vessel characteristics

| [mm] All | RD Average ± SD | MLD Average ± SD | Balloon Average ± SD | S-2-A Average ± SD |
|---|---|---|---|---|
| REFERENCE GROUP | 2.61 ± 0.59 | 2.83 ± 0.58 | 2.88 ± 0.34 | 1.12 ± 0.13 |
| P ANOVA | ns | ns | ns | ns |

Paclitaxel Concentration Analysis and Follow Up.

Within the entire follow-up period, neither death nor major adverse events cardiac events were noted. All animals remained in good general condition until euthanasia. Delivered paclitaxel concentrations by Reference group (reference balloon) were within the range of 1-12 μg/g, with steady decrease over 7 days (FIG. 1).

The balloons of both study groups delivered sirolimus in the range of 1-15 μg/g. At one hour follow up each balloon of a study group delivered sirolimus in the amount of 10-20 μg/g. At one day follow up in study group 1 sirolimus concentration found in the vessel was beyond 140 μg/g. On the other hand the second balloon set for the same follow up did not deliver sirolimusto the vessel wall. In the final observation sirolimus concentration was in the range of 1-1.5 μg/g in both studied groups (FIG. 1). None of the recorded differences were statistically significant.

The active agent residuals were significantly higher in the paclitaxel eluting balloons.

TABLE 14

Vessel intramural Paclitaxel and Sirolimus Concentration in μg/g (median and IQR)

| ug/g | Study group 1 N = 2 | Study group 2 N = 2 | Reference group N = 2 | ANOVA P |
|---|---|---|---|---|
| 1 hour | 12.8 [9.2:16.3] | 14.4 [12:16.7] | 10.1 [5.4:14.7] | Ns |
| 1 day | 63.1 [0:126.2] | 8.8 [2.6:15.1] | 6.65 [0-13.3] | Ns |
| 3 days | 0.65 [0:1.31] | 0.68 [0.15-1.22] | 1.5 [0.1:2.92] | Ns |
| 7 days | 1.27 [1.25:1.29] | 0.75 [0-1.5] | 1.65 [0-3.3] | Ns |

TABLE 15

Vessel intramural Paclitaxel and Sirolimus Concentration in μmol/l (median and IQR)

| μmol/l | Study group 1 N = 2 | Study group 2 N = 2 | Reference group N = 2 | ANOVA P |
|---|---|---|---|---|
| 1 hour | 15 [10.8:19.1] | 16.8 [14.1:19.6] | 11.8 [6.3:11.8] | Ns |
| 1 day | 73.8 [0:147.7] | 10.3 [3:17.6] | 7.8 [0:15.6] | Ns |
| 3 days | 0.7 [0:1.5] | 0.8 [0.17:1.4] | 1.8 [0.1:3.4] | Ns |
| 7 days | 1.5 [1.5:1.5] | 0.9 [0:1.8] | 1.9 [0:3.9] | Ns |

TABLE 16

Detailed concentration of sirolimus and paclitaxel

| no. | vessel | FU | Active agent | concentration [μmol/l] | concentration [μg/g] |
|---|---|---|---|---|---|
| 1 | RCA | 7 | Reference group | 3.87 | 3.30 |
| 1 | LAD | 7 | Study group 1 | 1.47 | 1.26 |
| 1 | LCX | 7 | Study group 2 | 0.00 | 0.00 |
| 2 | RCA | 7 | Study group 1 | 1.52 | 1.30 |
| 2 | LAD | 7 | Study group 2 | 1.76 | 1.50 |
| 2 | LCX | 7 | Reference group | 0.00 | 0.00 |
| 3 | RCA | 3 | Study group 2 | 0.17 | 0.15 |
| 3 | LAD | 3 | Reference group | 3.42 | 2.92 |
| 3 | LCX | 3 | Study group 1 | 1.54 | 1.32 |
| 4 | RCA | 3 | Study group 2 | 1.43 | 1.22 |
| 4 | LAD | 3 | Reference group | 0.11 | 0.10 |
| 4 | LCX | 3 | Study group 1 | 0.00 | 0.00 |
| 5 | RCA | 1 | Study group 2 | 17.64 | 15.07 |
| 5 | LAD | 1 | Study group 1 | 0.00 | 0.00 |
| 5 | LCX | 1 | Reference group | 0.00 | 0.00 |
| 6 | RCA | 1 | Reference group | 15.58 | 13.30 |
| 6 | LAD | 1 | Study group 1 | 147.77 | 126.18 |
| 6 | LCX | 1 | Study group 2 | 3.00 | 2.56 |
| 7 | RCA | 0 | Study group 1 | 10.80 | 9.22 |
| 7 | LAD | 0 | Reference group | 17.27 | 14.75 |
| 7 | LCX | 0 | Study group 2 | 14.05 | 12.00 |
| 8 | RCA | 0 | Study group 1 | 19.11 | 16.32 |
| 8 | LAD | 0 | Study group 2 | 19.59 | 16.72 |
| 8 | LCX | 0 | Reference group | 6.34 | 5.42 |

TABLE 17

Paclitaxel and Sirolimus residuals on balloons (μg/mm²)

| Factor | n | Mean | Different (P < 0.05) from factor nr |
|---|---|---|---|
| (1) STUDY GROUP 1 | 8 | 99.6 | (3) |
| (2) STUDY GROUP 2 | 8 | 119.2 | (3) |
| (3) REFERENCE GROUP | 8 | 198.8 | (1)(2) |

CONCLUSION

All tested balloons were easily introduced and deployed at study sites. No delivery or withdrawal problems occurred. The balloon diameters at nominal inflation reached their designed diameter. No adverse events were noted neither after procedures nor at follow up. On autopsy no macroscopic signs of myocardial infarction or inflammation within studied site were noted. It must be noted that due to very short term of observation and design of the study. the safety of studied balloon catheters was not an endpoint.

The baseline studied vessel characteristics between groups were similar with regard to reference diameter and minimal lumen diameter. Most importantly the stent to artery ratio of 1.1-1.2:1 resulted in similar overstretch between the studied groups. On the other hand due to very low number of tested balloons per group in each time point (n=2) a reproducible overstretch numerically was hard to achieve. All inflations were performed for 60 s and all balloon remained within the same period of time in circulation. Basing on previous studies this overstretch and inflation time should definitely provide proper and reproducible conditions for active agent delivery (1,2).

The paclitaxel concentrations delivered by the reference group were within 1-10 μg/g. This result is not comparable to currently clinically available paclitaxel eluting balloons which achieved higher tissue paclitaxel concentrations (2,3). Both tested sirolimus balloons delivered sirolimus to the vessel wall within the range of 1.5-20 μg/g. In all vessels sirolimus was found in 10-20 μg/g after 1 hour, therefore proving very good deliverability of sirolimus into the wall. In one tested study group 1 balloon the vessel concentration of sirolimus achieved an extraordinary result of 142 μg/g at 24 hour. Although the overstretch was high in this case (1.24:1) the second study group 1 balloon, deployed with the same inflation pressure and overstretch, did not deliver sirolimus to the vessel. Despite high numerical differences between study group 1 and 2 (63 vs. 8 μg/g) in this time point the result did not reach any statistical significance. At 7 days follow up in the study group 1 the concentrations were within 1.27 μg/g with a very low interquartile range and therefore are very reproducible.

This study is the first one that proved sirolimus deliverablity to the vessel wall (1) and therefore very promising. In a series of very few and rarely published reports sirolimus as a not liphophilic substance delivered from the balloon did not reach significant concentrations. Because the therapeutic or cytotoxic sirolimus concentrations after sirolimus eluting balloon angioplasty needed for neointima inhibition are unknown a long term tissue effects study is mandatory to prove its safety and efficacy in the porcine model of restenosis.

References for Example 16

1. Gray W A. Granada J F. Drug-coated balloons for the prevention of vascular restenosis. Circulation; 121:2672-80.
2. Posa A. Hemetsberger R. Petnehazy O. et al. Attainment of local drug delivery with padcitaxel-eluting balloon in porcine coronary arteries. Coron Artery Dis 2008; 19:243-7.
3. Scheller B. Speck U. Schmitt A. Bohm M. Nickenig G. Addition of paclitaxel to contrast media prevents restenosis after coronary stent implantation. J Am Coll Cardiol 2003; 42:1415-20.

Example 17

Proof-of-Principle Study for the Active Agent Transfer of a Sirolimus-Eluting Balloon in a Healthy Rabbit Model A sirolimus eluting balloon (3.0×20 mm) coated with a blend of sirolimus (3 μg/mm²), shellac (3 μg/mm²) and α-linolenic acid (1.5 μg/mm²) (in this example called DEB) was evaluated in regard to an effective sirolimus transfer into the arterial tissue during inflation of the balloon.

This study was carried out at the 'Deutsches Herzzentrum München'—clinic at the Technical University Munich. The appropriate approval of regional Bioethical Committee was obtained. HPLC-MS-based analysis for sirolimus content in tissue was conducted at ic42 Laboratory, University of Colorado, USA.

Study Design:

A total of 4 sirolimus eluting balloons were deployed in 2 healthy New Zealand White rabbits. For this purpose animals were anaesthetized with propofol and intra surgery analgesia was secured by repetitive boli of fentanyl. Animals were intubated, mechanically ventilated and at all times controlled for vital signs (pulse-oximetry and capnography). Anticoagulation was achieved by administration of 500 IU heparin and 40 mg aspirin i.v. Arterial access was conducted by cut down of the common carotid artery. A swan ganz catheter was advanced over the aortic arch under fluoroscopic guidance just before the bifurcation of the common iliac arteries of the abdominal aorta and an initial angiogram was performed. A guide wire was then placed in the external iliac artery. Wire guided balloon injury (POBA) with single balloon inflation [3.0×10 mm size balloon (Elect, Biotronik SE & Co. KG) at nominal pressure (7 atm) held for 30 seconds] within the middle portion of the external iliac artery was performed to induce arterial injury and facilitate sirolimus uptake into the vascular wall of healthy arteries. Afterwards the sirolimus eluting balloons were deployed covering the whole length of the induced lesion. The sirolimus eluting balloons were inflated at nominal pressure (6 atm) for 60 seconds. Five minutes after the procedure, a final angiogram was conducted and the animals were kept under anaesthesia until study termination at 1 hour. For study termination animals were euthanized with pentobarbital overdose i.v. Following euthanasia the abdomen was cut open and the abdominal aorta and caudal vena cava were exposed and accessed with arterial sheaths. Consecutively the vessels were flushed with 500 ml heparinized Ringers solution via the arterial sheath until blood clearance. Treated external iliac arteries were then carefully dissected, explanted and snap frozen in liquid nitrogen. Subsequently the treated iliac arteries (n=4) were stored at −70° C. until shipment on dry ice to the analytic laboratory. At the laboratory explanted treated vessels were weighed, homogenized and the undiluted homogenate was measured for sirolimus content. At all times, the batch samples were clearly identified and were processed on the same day using the same extraction method. All undiluted samples showed over detection range sirolimus content and were repeatedly measured after being diluted 1:10 and 1:20.

TABLE 18

Scheme of Ballon Dilatation Example 17

| Animal | | | Vessel | |
|---|---|---|---|---|
| Number | Animal ID | Time point | Left iliac artery | Right iliac artery |
| 1 | 7_12 | 1 hour | SIR 3 No. 27 | SIR 3 No. 26 |
| 2 | 8_12 | 1 hour | SIR 3 No. 28 | SIR 3 No. 29 |

Results:

Animals showed no sign of toxicity after sirolimus eluting balloon deployment and post expansion angiography revealed patent vessels and no sign of vessel wall dissection. Macroscopically, at the time of vessel explantation, there were also no signs of vessel trauma or dissection. The HPLC-based results show that there was remarkable sirolimus uptake into the vascular wall resulting in a mean concentration of 35.00±33.37 ng/mg. The tissue sirolimus concentrations ranged from 8 to 82 ng/mg.

TABLE 19

Tissue sirolimus content per treated vessel

| Group | Device Number | Balloon to artery ratio | Time point | Tissue sirolimus concentration (ng/mg) |
|---|---|---|---|---|
| SIR 3 | No. 26 | 1.1:1 | 1 hour | 36.13 |
| SIR 3 | No. 27 | 1.1:1 | 1 hour | 81.68 |

TABLE 19-continued

Tissue sirolimus content per treated vessel

| Group | Device Number | Balloon to artery ratio | Time point | Tissue sirolimus concentration (ng/mg) |
|---|---|---|---|---|
| SIR 3 | No. 28 | 1.1:1 | 1 hour | 14.10 |
| SIR 3 | No. 29 | 1.1:1 | 1 hour | 8.09 |

CONCLUSION

The current study aimed to examine tissue concentrations of sirolimus 1 hour after sirolimus eluting balloon deployment. The currently applied sirolimus eluting balloon resulted in significant sirolimus concentrations within the treated arteries. To the best of our knowledge this is the first sirolimus-eluting balloon capable to achieve arterial wall tissue concentrations of maximal 82 ng sirolimus/mg tissue. In this regard, the applied carrier formulation of shellac and omega fatty acids is a promising new coating technology for the delivery of sirolimus to the arterial tissue.

The invention claimed is:

1. A catheter balloon with a coating consisting of sirolimus, an omega-3 fatty acid and shellac.

2. The catheter balloon according to claim 1, wherein the omega-3 fatty acid is chosen from the group consisting of: eicosapentaenoic acid, eicosatrienoic acid, eicosatetraenoic acid, docosahexaenoic acid, hexadecatrienoic acid, stearidonic acid, heneicosapentaenoic acid, docosapentaenoic acid, tetracosapentaenoic acid, tetracosahexaenoic acid and α-linolenic acid as well as mixtures of the aforementioned fatty acids.

3. A balloon catheter comprising a catheter balloon according to claim 1.

* * * * *